(12) United States Patent
Kanegae et al.

(10) Patent No.: US 11,627,884 B2
(45) Date of Patent: Apr. 18, 2023

(54) BLOOD PRESSURE CALCULATION METHOD AND DEVICE

(71) Applicant: Health Sensing Co., Ltd., Hachioji (JP)

(72) Inventors: Masatomo Kanegae, Hachioji (JP); Kyuichi Niizeki, Yonezawa (JP)

(73) Assignee: Health Sensing Co., Ltd., Tokyo (JP)

( * ) Notice: Subject to any disclaimer, the term of this patent is extended or adjusted under 35 U.S.C. 154(b) by 559 days.

(21) Appl. No.: 16/607,000

(22) PCT Filed: Mar. 27, 2018

(86) PCT No.: PCT/JP2018/012321
§ 371 (c)(1),
(2) Date: Oct. 21, 2019

(87) PCT Pub. No.: WO2018/198637
PCT Pub. Date: Nov. 1, 2018

(65) Prior Publication Data
US 2020/0129078 A1    Apr. 30, 2020

(30) Foreign Application Priority Data

Apr. 24, 2017  (JP) .............................. JP2017-085021

(51) Int. Cl.
*A61B 5/021* (2006.01)
*A61B 5/00* (2006.01)

(52) U.S. Cl.
CPC ...... *A61B 5/02125* (2013.01); *A61B 5/02116* (2013.01); *A61B 5/7253* (2013.01); *A61B 5/6801* (2013.01)

(58) Field of Classification Search
None
See application file for complete search history.

(56) References Cited

U.S. PATENT DOCUMENTS 6,027,455 A * 2/2000 Inukai ................ A61B 5/02125
                                                                    600/485
7,455,643 B1 * 11/2008 Li .......................... A61B 5/022
                                                                    600/490

(Continued)

FOREIGN PATENT DOCUMENTS

CN        105072984      11/2015
CN        106028918      10/2016

(Continued)

OTHER PUBLICATIONS

English Translation of CN 109069031 (Year: 2016).*

(Continued)

*Primary Examiner* — Jacqueline Cheng
*Assistant Examiner* — Jairo H Portillo
(74) *Attorney, Agent, or Firm* — Jeffrey I. Auerbach; Auerbach LLC

(57) ABSTRACT

[Subject] Non-invasive method for estimating blood pressure without a cuff and a device for the blood pressure estimation
[Resolution means] Systolic blood pressure (EBP) is estimated according to $EBP=\beta_1 \cdot P1+\beta_2 \cdot P2+\beta_0$ ($\beta_1$, $\beta_2$, and $\beta_0$ are coefficients) where parameter P1, which is related to pulse transit time (PTT), and parameter P2, which is related to stroke volume based on pulse waves, are variables.

14 Claims, 14 Drawing Sheets

(56) References Cited

U.S. PATENT DOCUMENTS

| | | | | |
|---|---|---|---|---|
| 2009/0151478 A1* | 6/2009 | Shimomoto | ........... | A61B 5/021 |
| | | | | 73/862.626 |
| 2009/0326393 A1* | 12/2009 | Sethi | ................. | A61B 5/02108 |
| | | | | 600/494 |
| 2016/0345844 A1 | 12/2016 | McCombie et al. | | |

FOREIGN PATENT DOCUMENTS

| | | | | |
|---|---|---|---|---|
| CN | 109069031 | * | 10/2016 | ............. A61B 5/021 |
| CN | 107106046 | | 8/2017 | |
| EP | 956817 | | 11/1999 | |
| EP | 3199101 | | 8/2017 | |
| JP | 10-295657 | | 11/1998 | |
| JP | 2000-023927 | | 1/2000 | |
| JP | 2016-83007 | | 5/2016 | |
| JP | 5940725 | | 5/2016 | |
| JP | 2016-516503 | | 6/2016 | |
| KR | 10-2017-0082453 | | 7/2017 | |
| WO | WO 2014/147554 | | 9/2014 | |
| WO | WO 2015/120330 | | 8/2015 | |
| WO | WO 2017/098739 | | 6/2017 | |

OTHER PUBLICATIONS

WIPO International Search Report, PCT/JP2018/012321 (dated Jun. 28, 2018) 3 pages (English Translation 2 pages).
WIPO Written Opinion, PCT/JP2018/012321 (dated Jun. 28, 2018) 5 pages (English Translation 5 pages).

* cited by examiner

BLOOD PRESSURE CALCULATION METHOD AND DEVICE

CROSS-REFERENCE TO RELATED APPLICATIONS

This application is a § 371 National Stage Application of PCT/JP2018/012321 (filed on Mar. 27, 2018; pending), which application claims benefit of JP Patent Application No. 2017-085021 (filed on Apr. 24, 2017). Each of these applications is hereby incorporated by reference in its entirety.

FIELD OF THE INVENTION

This invention is related to a non-invasive method for estimating blood pressure without a cuff and a device for the blood pressure estimation.

BACKGROUND OF THE INVENTION

Blood pressure is the force of flowing blood, which is sent by the heart as a pump to circulate throughout the body, on the walls of the blood vessels. The blood pressure reaches the highest when the cardiac ventricle constricts, and it reaches the lowest when the heart dilates. Conventionally, blood pressure has been measured by various methods. In the indirect method, generally, a cuff wrapped around the arm is inflated to compress the arteries to stop the blood flow transiently, and then when it is deflated, blood pressure is measured by detecting sounds or vibrations of re-flowing blood. The measurement with the cuff, however, has the following problems: the device is large; a subject is required to be restrained and kept still, and thus continuous measurement or routine monitoring is not possible; because the cuff operation takes more than 10 seconds, only the average during the measurement can be determined, but a rapid change in blood pressure cannot be detected; and the cuff's compression may cause pain depending on its strength.

In recent years, methods for determining blood pressure using biometric electrocardiogram signal (ECG signal) or pulse wave signal (pulse plethysmograph signal or PPG signal) are being studied. For instance, a reference patent 1 has disclosed a method for estimating blood pressure by attaching a pair of electrodes and a pulse wave sensor to a subject. In this method, the former device measures the impedance and ECG signals, while the latter one measure pulses waves, and the acquired data are applied to the computing formulas (1) to (4) below to determine the estimated blood pressure (EBP).

$$EBP = \alpha \cdot PTT + \beta \cdot a1 + \gamma \cdot Z + \delta \quad (1)$$

$$EBP = \alpha \cdot PTT/UT + \beta \cdot d + \gamma \cdot Z + \delta \quad (2)$$

$$EBP = \alpha \cdot PTT/UT + \beta \cdot a1 + \gamma \cdot Z + \delta \quad (3)$$

$$EBP = \alpha \cdot PTT/UT + \beta QT + \gamma \cdot Z + \delta \quad (4)$$

In the above formulae (1) to (4), where $\alpha$, $\beta$, $\gamma$, and $\delta$ are coefficients; PTT is pulse transit time; a1 is a wave height of the first peak in a velocity pulse wave (the first derivative of PPG signal); Z is impedance; UT is the time between the foot point and the first peak of a pulse wave; d is a wave height of the fourth peak in an acceleration pulse wave (the second derivative of PPG signal); and QT is the time interval between the foot point of a ventricular pulse and the first peak after the pulse.

LEADING TECHNICAL REFERENCE

Reference Patent

[Reference Patent 1] PD 2008-279185 Official Gazette

SUMMARY OF THE INVENTION

Issues to be Resolved by the Invention

The method described in Reference Patent 1 gives EBP a substantial error, and thus a more accurate pressure estimation method was desired. This invention is intended to offer a non-invasive method for estimating blood pressure without a cuff, different from ones based on conventional technologies, and a device for the blood pressure estimation.

Means to Resolve the Subject

To resolve the above challenge, the blood pressure estimation method of this invention estimates systolic blood pressure (estimated systolic blood pressure or EBP) according to $EBP = \beta_1 \cdot P1 + \beta_2 \cdot P2 + \beta_0$ or $EBP = \beta_1 \cdot 1/P1 + \beta_2 \cdot P2 + \beta_0$ ($\beta_1$, $\beta_2$, and $\beta_0$ are coefficients) where parameter P1, which is related to PTT, and parameter P2, which is related to stroke volume based on pulse waves, are variables.

Furthermore, it is desirable to establish the above blood pressure estimation method as follows: measured blood pressures are obtained from the subject under varied loads, while the above parameter P1 and parameter P2 are measured; the measured parameter values are then substituted into the above formula to give coefficients β1, β2, and β0 that allow approximation to the change in measured blood pressure.

A blood pressure estimation method other than this invention estimates systolic blood pressure (EBP) according to $EBP = \beta1 \cdot P1 + \beta2 \cdot P2 + \beta3 \cdot P3 + \beta0$ or $EBP = \beta1 \cdot 1/P1 + \beta2 \cdot P2 + \beta3 \cdot P3 + \beta0$ (β1, β2, β3, and β0 are coefficients) where parameter P1, which is related to PTT, parameter P2, which is related to stroke volume based on pulse waves, and parameter P3, which is related to systole duration based on pulse waves, are variables.

Furthermore, it is desirable to establish the above blood pressure estimation method as follows: measured blood pressures are obtained from the subject under various load conditions, while the above parameter P1, parameter P2, and parameter P3 are measured; the measured parameter values are then substituted into the above formula to give coefficients $\beta_1$, $\beta_2$, $\beta_3$, and $\beta_0$ that allow approximation to the change in measured blood pressure.

Furthermore, in the blood pressure estimation method, parameter P2 may be pulsatile systolic area (PSA) defined by the area under the curve above a horizontal line drawn from the foot point and bounded by a vertical line through the dicrotic notch of a pulse wave expressed in signal waveform, a part of the PSA, area including the PSA, or area during a period pre-determined to include at least a part of the first peak of a pulse wave. Furthermore, the DN may be a position where the differentiated waveform of a pressure pulse wave peaks between its minimum point (trough) and the next pulse. In addition, parameter P2 may be a ratio of the mean first area during a period including at least a part of the first peak of a pulse wave to the mean second area during a part of the remaining period for the concerned pulse wave.

Furthermore, in the above blood pressure estimation method, it is desirable to acquire pulse waves from a subject at the sampling frequency ≥500 Hz or ≥1 kHz. In addition, a change in relative systolic blood pressure (EBP) may be calculated using the coefficient β0 as a pre-determined fixed value.

In addition, the device for the blood pressure estimation in this invention is characterized by the following components: the first biosignal detection means and second biosignal detection means that detect biosignals on a subject; P1 calculation means that calculates parameter P1, which is related to PTT, from biosignals acquired through the preceding first biosignal detection means and second biosignal detection means; P2 calculation means that calculates parameter P2, which is related to stroke volume based on pulse waves, from biosignals acquired through either or both of the preceding first biosignal detection means and second biosignal detection means; and the blood pressure estimation part that estimates systolic blood pressure (EBP) according to a formula, $EBP=\beta_1 \cdot P1+\beta_2 \cdot P2+\beta_0$ or $EBP=\beta_1 \cdot 1/P1+\beta_2 \cdot P2+\beta_0$ ($\beta_1$, $\beta_2$, and $\beta_0$ are coefficients) where the parameter P1 calculated by the preceding P1 calculation means and parameter P2 calculated by the preceding P2 calculation means are variables.

In addition, the other device for the blood pressure estimation in this invention is characterized by the following components: the first biosignal detection means and second biosignal detection means that detect biosignals on a subject; P1 calculation means that calculates parameter P1, which is related to PTT, from biosignals acquired through the preceding first biosignal detection means and second biosignal detection means; P2 calculation means that calculates parameter P2, which is related to stroke volume based on pulse waves, from biosignals acquired through either or both of the preceding first biosignal detection means and second biosignal detection means; P3 calculation means that calculates parameter P3, which related to systole duration based on pulse waves from biosignals acquired through either or both of the preceding first biosignal detection means and second biosignal detection means; and the blood pressure estimation part that estimates systolic blood pressure (EBP) according to a formula, $EBP=\beta_1 \cdot P1+\beta_2 \cdot P2+\beta_3 \cdot P3+\beta_0$ or $EBP=\beta_1 \cdot 1/P1+\beta_2 \cdot P2+\beta_3 \cdot P3+\beta_0$ ($\beta_1$, $\beta_2$, $\beta_3$, and $\beta_0$ are coefficients) where the parameter P1 calculated by the preceding P1 calculation means, parameter P2 calculated by the preceding P2 calculation means, and parameter P3 calculated by the preceding P3 calculation means are variables.

Furthermore, in the above device for the blood pressure estimation, at least either of the preceding first biosignal detection means and second biosignal detection means is desired to be a pulse wave sensor that acquires biosignals including pulse waves. Furthermore, the above pulse wave sensor may be a sheet-type piezoelectric sensor or wearable sensor. In addition, in the above pulse wave sensor, it is desirable to acquire pulse waves from a subject at the sampling frequency ≥500 Hz or ≥1 kHz.

Effects of the Invention

With the blood pressure estimation method and device for the blood pressure estimation of this invention, highly accurate EBP can be determined because blood pressure is calculated using parameter P1, related to PTT highly correlated to blood pressure, and parameter P2, related to the stroke volume of pulse waves, as variables. The blood pressure estimation method of this invention can calculate blood pressure only from data on 2 pulse waves or the pulse waves and heart beating, allowing non-invasive EBP determination without a cuff. In addition, data on 2 pulse waves or the pulse waves and heart beating can be acquired real time and without restriction. This invention enables routine real-time blood pressure monitoring. Furthermore, in principle, blood pressure for each beat can be calculated, allowing measurement of respiratory changes in blood pressure.

DESCRIPTION OF EMBODIMENTS OF THE INVENTION

Figure 1:
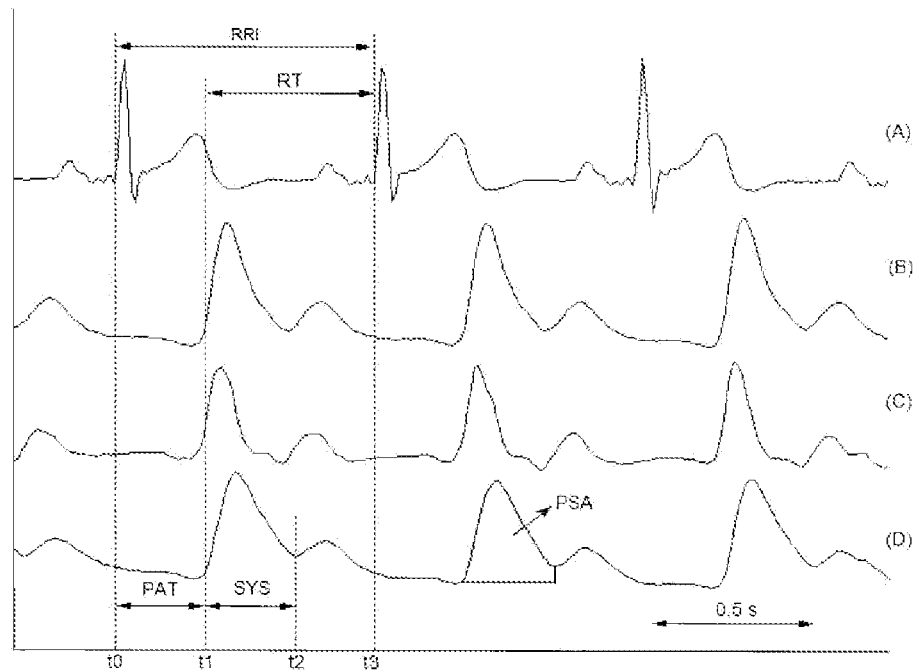
FIG. 1: (A) ECG; (B) blood pressure; (C) digital pulse waves; and (D) integrated waveforms of digital pulse waves.

Brief Description about Blood Pressure Estimation Method of this Invention

The blood pressure estimation method of this invention is based on a finding that parameter P1, which is related to PTT, and parameter P2, which is related to stroke volume based on pulse waves are correlated to systolic blood pressure (SBP) and thus estimates SBP by applying the basic principle in which at least parameter P1 and parameter P2 are used as variables. Pulse waves are defined as waves that represent changes in internal pressure of the artery in response to cardiac ejection of blood and propagate through the wall of blood vessel. Pulse wave signals (PPG signals) can be obtained by measuring changes in pressure or volume of the vessel system. Signals obtained by measuring changes in pressure are named as pressure pulse waves, and ones by measuring changes in volume are named as volume pulse waves. In addition, the first derivative waves of the pressure pulse waves or volume pulse waves are named as velocity pulse waves, and the second derivative waves are named as acceleration pulse waves. Furthermore, the integrated waveforms of pressure pulse wave or volume pulse waves are named as integrated pulse waves. In this specification, "pulse waves" include pressure pulse wave, volume pulse waves, velocity pulse waves, acceleration pulse waves, and integrated pulse waves. Pulse waves are detected as not only signals obtained by measurement, differentiation, or integration but also signal waveforms obtained through various processing procedures on these signals such as translation, noise reduction processing, frequency extraction and analysis processing, and sampling processing. Stroke volume is the volume of blood ejected into the aorta by one contraction of the heart.

Parameter P1 may be pulse transit time (PTT) or time for a pulse wave to transit a distance specified by given 2 points, pulse arrival time (PAT) or time from start of the heartbeat generating a pulse wave to arrival of the pulse wave at the measurement point, or pulse wave velocity (PWV) or velocity of a pulse wave propagation. PTT can be calculated, for instance, from a time difference between positions of 2 pulse waves measured at 2 points (or more) with respect to the same beat in the same time series, that is, a time difference between peaks of the pulse waves with respect to the same beat. PAT can be calculated from a time difference between the signal of start of a heartbeat and position of 1 pulse wave measured at 1 given point (or more) with respect to the same beat in the same time series, for instance, a time difference between R wave in ECG and position of the peak of a pulse wave with respect to the same beat. PWV can be calculated according to either formula of distance between measurement position/PTT or distance between measurement position/(PAT−PEP), where PEP is pre-ejected period. As long as measurement positions of pulse waves are constant, the distance remains unchanged, and thus relative changes in PWV can be calculated from PTT or PAT.

Parameter P2 is related to a stroke volume in pulse waves. A pulse wave sharply raises upon opening of the aortic valve in the heart, form dicrotic notch (DN) upon its closing, and then slowly declines. That is, time from the foot point of the pulse wave peak to the DN corresponds to the time that the heart is sending blood into the artery. The waveform of the pulse wave during the concerned time is related to stroke volume. Parameter P2 may be, for instance, area under the curve above a horizontal line drawn from the foot point and bounded by a vertical line through the dicrotic notch of a pulse wave expressed in signal waveform, a part of the PSA, or area including the PSA. A part of the PSA may apply to the case, for instance, where the duration used in the area calculation starts slightly after the foot point of the first peak of a pulse wave or ends slightly before the DN. An area including the PSA may apply to the case, for instance, where the duration used in the area calculation starts slightly before the foot point of the first peak or ends slightly after the DN. Waveforms without definite DN may also occur in the cases, for instance, where the measurement point for pulse waves is far from the heart or something abnormal is involved. In these cases, an area of a certain duration pre-determined so that at least a part of the first peak of a pulse wave will be included may be used as stroke volume-related parameter P2. The pre-determined duration may be, for instance, a defined period from the foot point of a pulse wave to a timepoint after a specified duration including the peak, an undefined period from the foot point of a pulse wave to a timepoint after a specified duration from the peak top (because time to the peak top differs from a pulse wave to a pulse wave, it is not defined), or an undefined period from the foot point of a pulse wave to a timepoint after a specified duration from the trough within the same beat expressed in differentiated waveforms of pressure pulse waves. The pre-determined duration may be established based on the age, body weight, or sex, but for improved accuracy, it is desirable to establish a specified duration by calculating the timing of the DN from measured pulse waves, because it is based on biological information of the subject. In addition, to identify timing of the foot point, top, and DN of a peak, pulse waves may be obtained by signal processing such as integration, differentiation, and Hilbert transformation. For instance, as marked with Δ in a waveform in FIG. 9 (C), the DN may be identified based on the peak position of a differentiated waveform from its trough to the next pulse.

Furthermore, parameter P2 may be a ratio of the mean first area during a period including at least a part of the first peak of a pulse wave to the mean second area during a part of the remaining period for the concerned pulse wave. For instance, parameter P2 may be a ratio of the mean (S1/T1) area S1 (=PSA) under the curve from the foot point of the first peak to the DN of a pulse wave expressed in signal waveform to the mean (S2/T2) area S2 under the curve from the DN to the foot point of the next pulse It is desirable to use PSA as the first area including at least a part of the first peak of a pulse wave, but area including a part of the PSA or area including the PSA may be used. The second area covering at least a part of the remaining period for the concerned pulse wave may be either whole or a part of the remaining whole area (area from the end timepoint of the first area to time after a specified duration or area from the end timepoint of the first area to time after a specified duration from the start of the next pulse wave). Parameter P2 may be a ratio of the mean first area to the mean second area of each pulse wave, which allows normalization of the parameter P2 within each pulse wave so that this parameter can be used more widely. For instance, even if signal intensity (amplitude) is changed due to a difference in biosignal measurement condition, ambient environment, or device setting, blood pressure can be calculated using a ratio of the mean first area to the mean second area of each pulse wave.

EBP can be calculated by substituting parameter P1 and parameter P2 into the following formula (5) as variables. If PTT or PAT is used as P1, the formula (6) may be applied as P1 is inversely proportional to blood pressure. In formulae (5) and (6), $\beta_1$, $\beta_2$, and $\beta_0$ are coefficients, and the blood pressure estimation method of this invention preferably has a step for establishment of the coefficients.

$$EBP = \beta_1 \cdot P1 + \beta_2 \cdot P2 + \beta_0 \quad (5)$$

$$EBP = \beta_1 \cdot 1/P1 + \beta_2 \cdot P2 + \beta_0 \quad (6)$$

Because coefficients $\beta_1$, $\beta_2$, and $\beta_0$ differ from an individual to an individual, it is desirable to determine the adjusted coefficients in advance by measuring actual blood pressure of the subject (measured blood pressure). Combinations of typical coefficients for each of conditions such as age, sex, body weight, and shape of pulse waves may be prepared in the device so that it can select a coefficient value typical for the input condition and apply to the calculation. Coefficient $\beta_0$ is required for estimation of absolute blood pressure, but not essential for relative determination of an increase or decrease in blood pressure. For instance, a pre-determined fixed value B (0 [zero] for instance) may be used as coefficient $\beta_0$ instead of the estimated coefficient $\beta_0$ to calculate a relative change in blood pressure according to either formula, $EBP = \beta_1 \cdot P1 + \beta_2 \cdot P2 + B$ or $EBP = \beta_1 \cdot 1/P1 + \beta_2 \cdot P2 + B$ (B is a pre-determined value).

For instance, coefficients $\beta_1$, $\beta_2$, and $\beta_0$ may be determined as follows: measured blood pressures are obtained from the subject under various load conditions using a blood pressure capturing means, while parameter P1, which is related to PPT, and parameter P2, which is related to the stroke volume based on PPG signals, are measured; and then these coefficients are determined so that a change obtained by substitution of the measured parameter P1 and parameter P2 values into the formula (5) or (6) is approximated to that in measured blood pressure. Loads given to the subject may be physical or psychological stress through exercise, standing, Valsalva maneuver, mental load. An effect of such load on blood pressure is evaluated by changing strength of the stress. Exercise loads may be, for instance, handgrip exercise and exercise using a machine (walking on a treadmill, riding on a stationary bike, etc.). Standing load may be, for instance, pose changes from sitting to standing and from laying to sitting. Valsalva maneuver is an action of breathing forcefully against a closed airway. In addition, mental loads may be, for instance, calculation, mental arithmetic, memorization, and reading. The desirable load changes blood pressure of the subject by at least $\geq 10$ mmHg, and more desirably $\geq 20$ mmHg. The desirable load given to the subject has a limited direct impact on measured blood pressure and measurement of pulse waves. For instance, in the case of handgrip exercise, vibration and compression of muscles in the arm may affect blood pressure and pulse waves, and thus it is desirable to measure these values on a body site other than the exercising arm (for instance, the opposite arm or leg).

FIG. 1 explains various parameters using data obtained in the same time series: (A) waveforms of 3 beats in ECG; (B) finger blood pressure measured with a volume-compensated sphygmomanometer; (C) finger pulse waves; and (D) integrated waveforms of finger pulse waves obtained by integration with respect to a time constant of 0.1 seconds. In FIG. 1, t0 is the timepoint of the foot point of QRS wave of ECG (A); t1 is the timepoint of the foot point of the first peak of integrated pulse waves (D); t2 is the timepoint of the DN of integrated pulse waves (D), which almost agrees with the DN of blood pressure (B); and t3 is the timepoint of the foot point of next QRS wave of ECG (A). Of integrated pulse waves (D), t1 is associated with opening of the aortic valve; the interval between t1 and t2 or timepoint of the DN corresponds to systole of the heart; and the period after the DN corresponds to diastole of the heart. Therefore, a time difference from t0, timepoint of the foot point of QRS wave of ECG (A), to t1 of integrated pulse waves (D) is pulse arrival time (PAT) at the position of measuring pulse waves; the period between t1 and t2 corresponds to a systole (SYS) of the heart based on pulse waves. An interval between t0 and t3 in ECG (A) is a RR interval (RRI) between QRS waves, and RT is obtained by subtracting PAT from RRI. In addition, the area under the curve during a systole (t1 to t2) in integrated pulse waves (D) is PSA, which is related to stroke volume. In the case where the second pulse waves are measured at the other position, a time difference between the foot point of the first peak in integrated waveforms of the second pulse waves and t1, the foot point of the first peak in integrated pulse waves (D) corresponds to pulse transit time (PTT). PTT may be calculated from a time difference between peak tops or between DNs instead of between the foot points of the first peaks.

Figure 2:
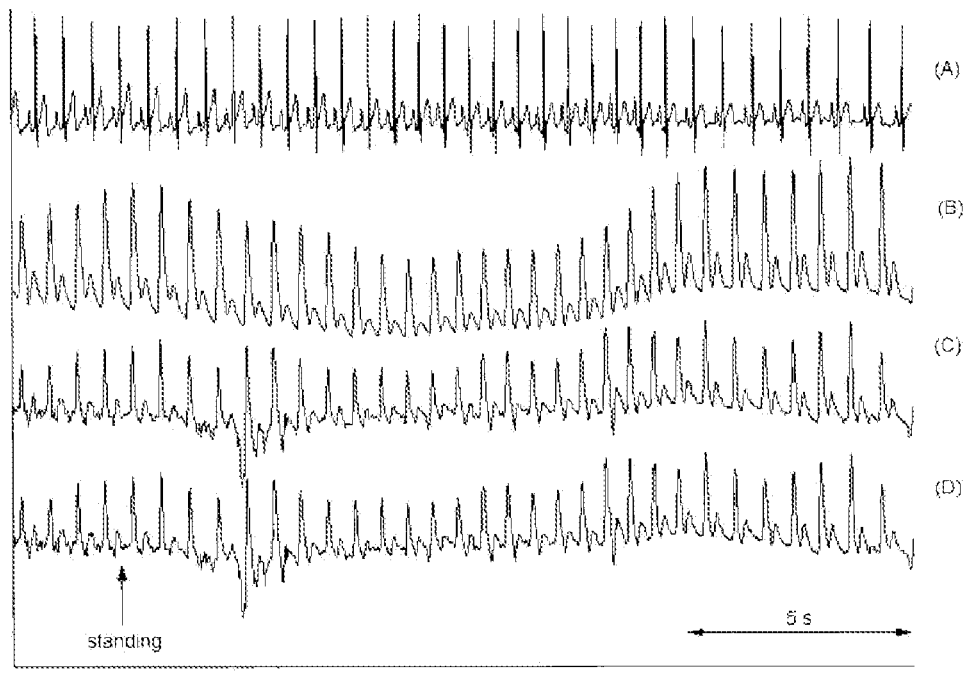
FIG. 2: (A) Measured ECG; (B) blood pressure; (C) digital pulse waves; and (D) integrated waveforms of digital pulse waves.

FIG. 2 shows data obtained in the same time series and processed data: (A) measured ECG; (B) blood pressure; (C) digital pulse waves; and (D) integrated waveforms of digital pulse waves in which the vertical axis and horizontal axis indicate the intensity and time, respectively. ECG in (A) was obtained through bipolar leads for ECG attached to the chest of the subject. Furthermore, measured blood pressure in (B) was obtained at the same time. Blood pressure in (B) was continuously measured through a cuff of the volume-compensated sphygmomanometer attached to the index finger of the subject. Pulse waves (C) were pressure pulse waves obtained through a piezoelectric sensor closely attached to the tip of the middle finger of the subject. Integrated waveforms (D) are waveforms obtained by integration of finger pulse waves in (C) with respect to a time constant of 0.1 seconds.

Figure 3:
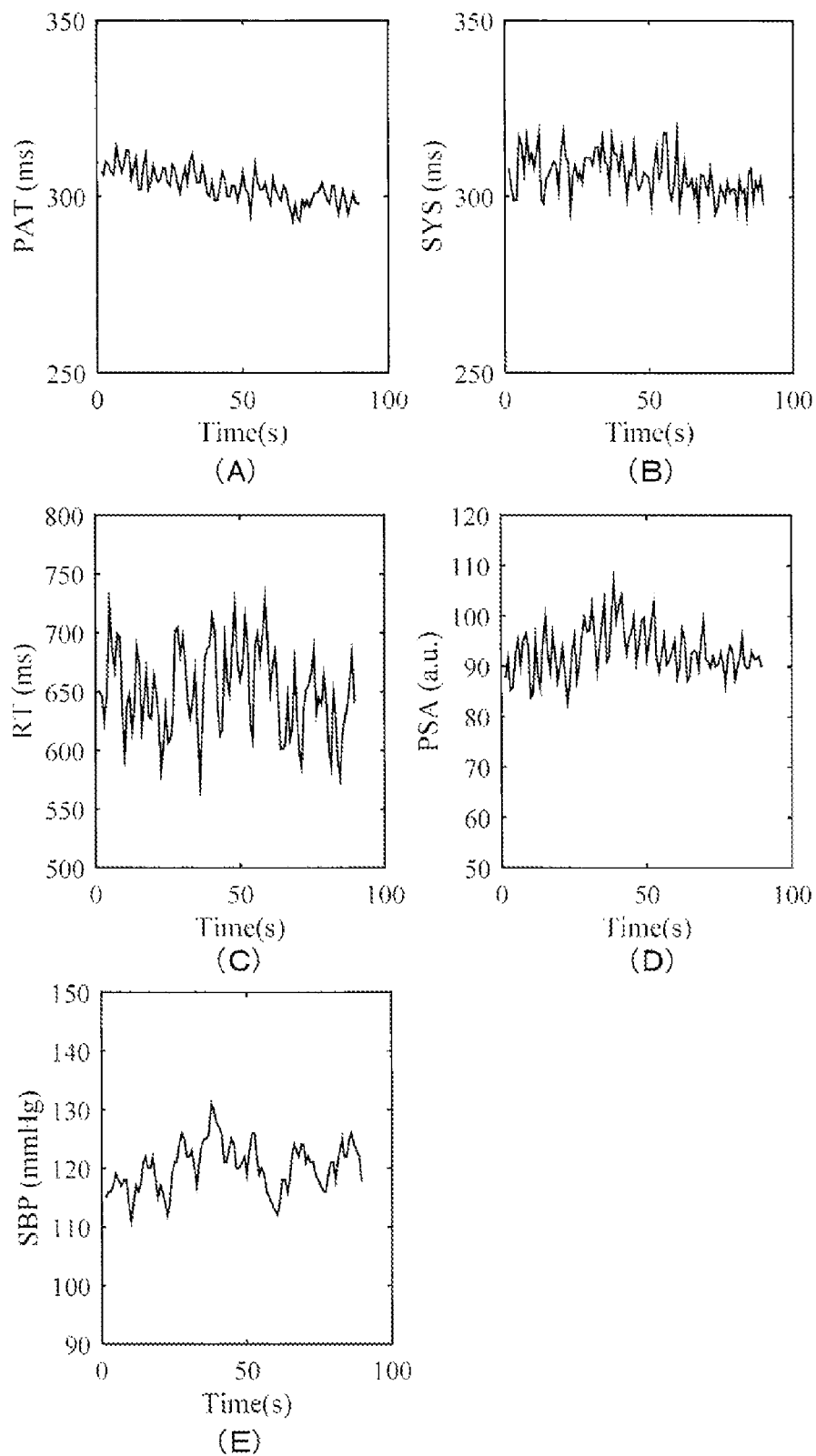
FIG. 3: (A) to (D) Changes of each parameter; and (E) measured systolic blood pressure.

FIG. 3 (A) to (D) shows changes in parameters calculated from waveforms in pulse waves in (D) and ECG in (A) under FIG. 2 over time, and FIG. 3 (E) shows measured systolic blood pressure. More specifically, FIG. 3 presents the following changes in the same time series: (A) PAT; (B) SYS; (C) RT; (D) PSA; (E) measured SBP.

Figure 4:
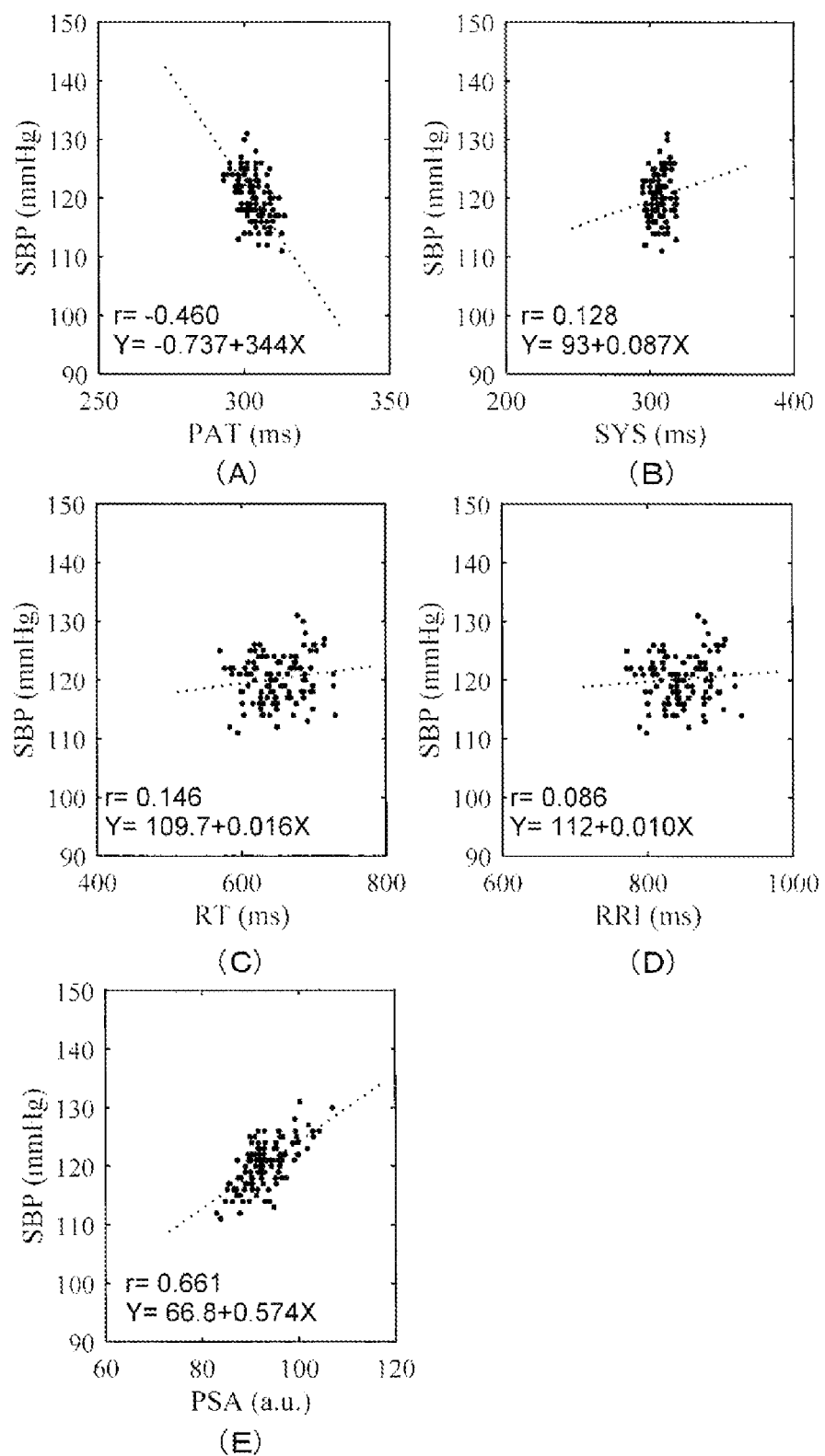
FIG. 4: Correlation diagram between measured systolic blood pressure (SBP) and parameter value (PAT, SYS, RT, RRI, PSA).

FIG. 4 shows correlation diagrams between measured SBP and parameter value (PAT, SYS, RT, RRI, and PSA). In FIG. 4, the vertical axis indicates measured SBP, while the horizontal axis indicates each of the above parameters, and the regression line and correlation coefficient (r) are presented. FIG. 4 (A) shows a correlation diagram between measured SBP and PAT, and the correlation coefficient (r) was 0.46 with P value <0.01, indicating a significant correlation with the significance level <1%. FIG. 4 (B) shows a correlation diagram between measured SBP and SYS, and the correlation coefficient (r) was 0.128 with P value of 0.192, ruling out the significant correlation. FIG. 4 (C) shows a correlation diagram between measured SBP and RT (interval between t1 and t3 in FIG. 1) and the correlation coefficient (r) was 0.146 with P value of 0.138, ruling out the significant correlation. FIG. 4 (D) shows a correlation diagram between measured SBP and RRI (interval between t0 and t3 in FIG. 1) and the correlation coefficient (r) was 0.086 with P value of 0.384, ruling out the significant correlation. FIG. 4 (E) shows a correlation diagram between measured SBP and PSA, and the correlation coefficient (r) was 0.661 with P value <0.01, indicating a significant correlation with the significance level <1%. FIG. 4 reveals that PAT and PSA correlate to measured SBP.

Figure 5:
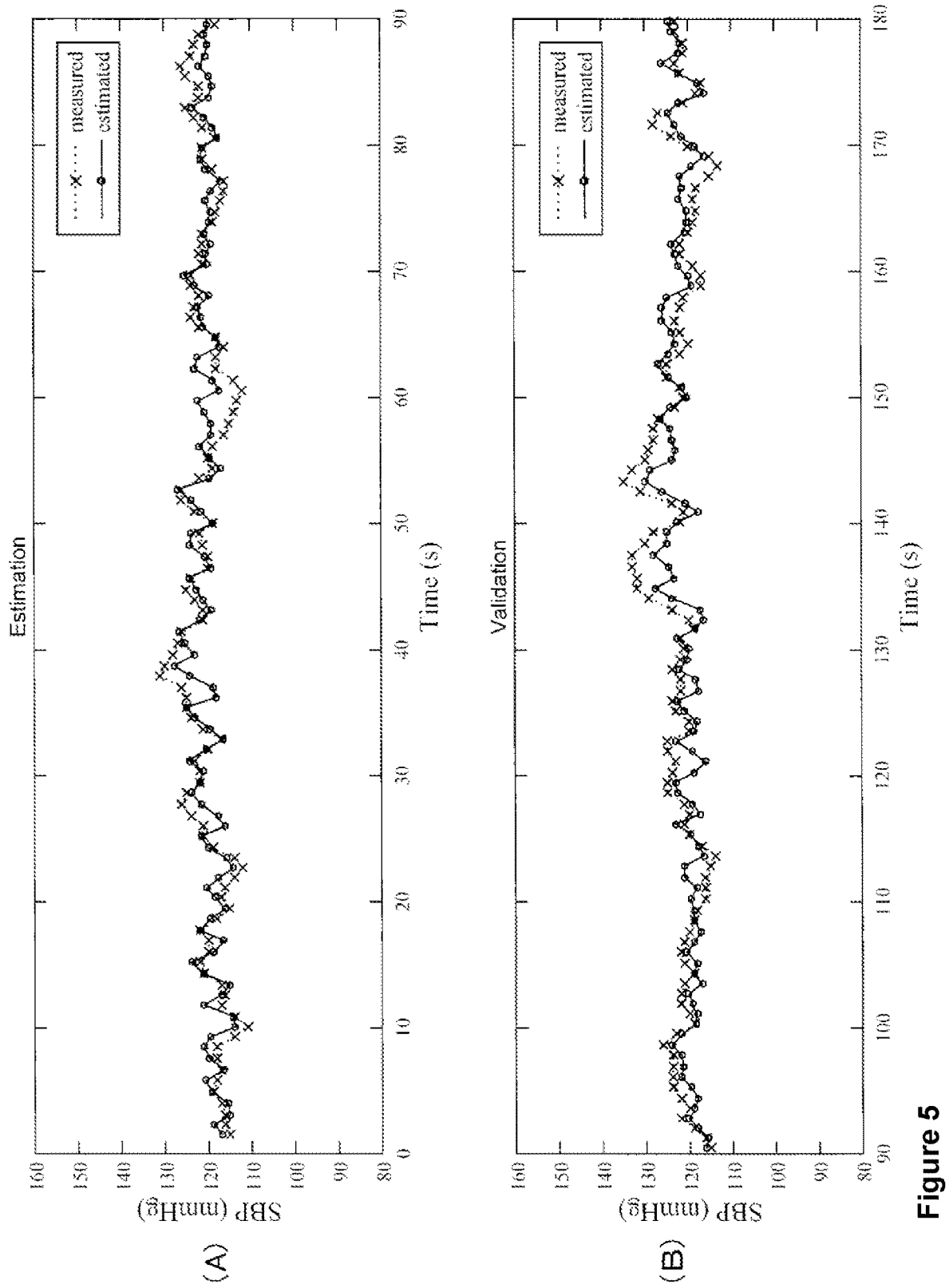
FIG. 5: Measured systolic blood pressure (dotted line) and estimated systolic blood pressure (EBP) (solid line) calculated according to the formula (5).

FIGS. 5 (A) and (B) shows measured SBP (dotted line) and estimated SBP (EBP) (solid line) calculated according to the formula (5). In FIG. 5 (A), EBP (solid line) is a result from approximation to measured SBP (dotted line) between 0 and 90 seconds by adjusting coefficients $\beta_1$, $\beta_2$, and $\beta_0$ based on PAT and PSA measured in the same time series. That is, in the formula (5), measured SBP was substituted for EBP, and measured PAT and PSA were substituted for parameter P1 and parameter P2, respectively. To establish the formula (5) wherever possible, coefficients $\beta_1$, $\beta_2$, and $\beta_0$ were adjusted. Thereby, the coefficients $\beta_1$, $\beta_2$, and $\beta_0$ were estimated for the subject individually. FIG. 5 (B) shows results from validation of the formula (5) using the above estimated coefficients $\beta_1$, $\beta_2$, and $\beta_0$. In this validation, measured PAT and PSA between 90 and 180 seconds were substituted into the formula (5) (with the estimated coefficients $\beta_1$, $\beta_2$, and $\beta_0$) to calculate EBP (solid line). FIG. 5 (B) shows that waveforms of EBP (solid line) calculated according to the formula (5) are close to those of measured SBP, demonstrating that the formula (5) is capable of estimating blood pressure of a subject.

Figure 6:
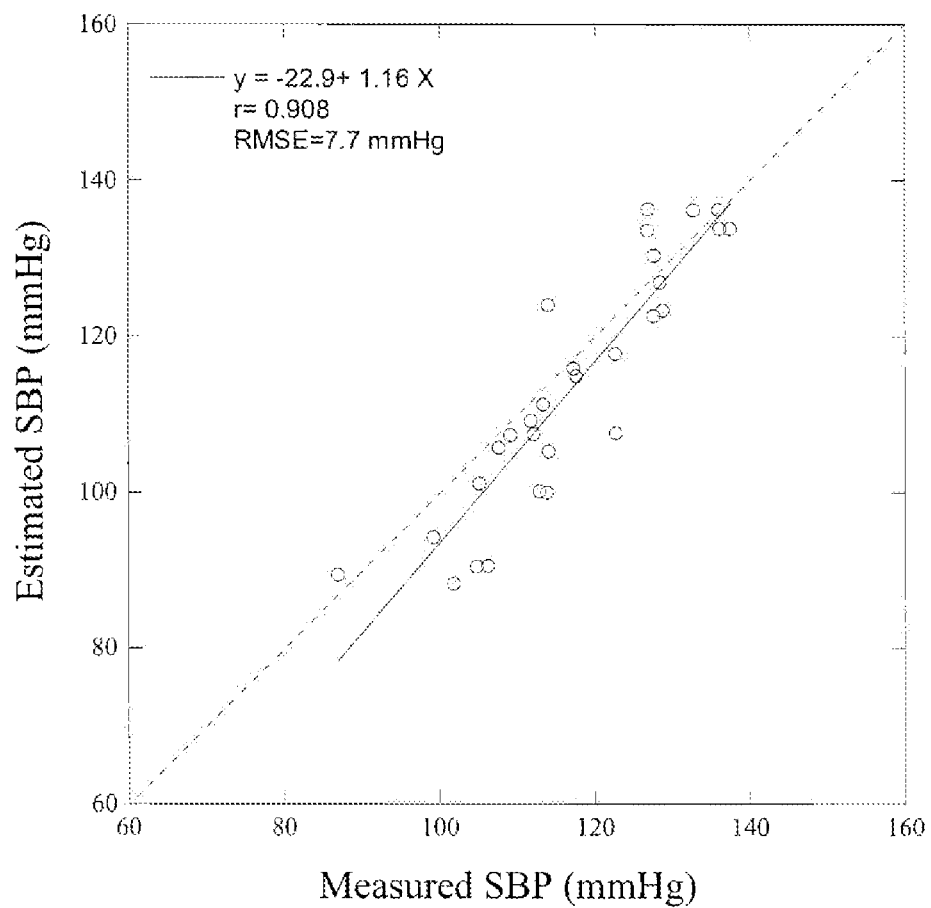
FIG. 6: Correlation diagram between mean measured systolic blood pressure (horizontal axis) and mean estimated systolic blood pressure (vertical axis) (n=29).

FIG. 6 shows a correlation diagram between mean measured SBP (horizontal axis) and mean EBP (vertical axis) based on results from an experiment with 29 measurements in 9 subjects, which was conducted as done for experiments in FIG. 2 or 5. The correlation coefficient r was 0.908, and P value <0.01, indicating a significant correlation. In addition, the root mean square error (RMSE) was 7.7 mmHg. As shown above, FIG. 6 has demonstrated that EBP calculated according to the formula (5) is strongly correlated to measured SBP.

Because the subsequent studies showed that SYS was correlated to measured SBP depending on a subject or measurement conditions, parameter P3 may be used as a variable in addition to parameter P1 and parameter P2 in estimation of SBP. Parameter P3 may be, for instance, an interval between the foot point of the first peak (t1) and DN (t2) in integrated pulse waves (D) under FIG. 1. In addition, waveforms without definite DN may also occur in the cases, for instance, where the measurement point for pulse waves is far from the heart or something abnormal is involved. In these cases, a certain duration pre-determined so that at least a part of the first peak of a pulse wave will be included may be used as parameter P3. The pre-determined duration may be, for instance, a period from the foot point of a pulse wave to a timepoint after a specified duration including the peak, a period from the foot point of a pulse wave to a timepoint after a specified duration from the peak top, or a period from the foot point of a pulse wave to a timepoint after a specified duration from the trough within the same beat expressed in differentiated waveforms of pressure pulse waves. The pre-determined duration may be established based on the age, body weight, or sex, but for improved accuracy, it is desirable to establish a specified duration by calculating the timing of the DN from measured pulse waves, because it is based on biological information of the subject.

EBP can be calculated by substituting parameter parameter P1, parameter P2, and parameter P3 into the following formula (7) as variables. If PTT or PAT is used as P1, the formula (8) may be applied as P1 is inversely proportional to blood pressure. In formulae (7) and (8), $\beta_1$, $\beta_2$, $\beta_3$, and $\beta_0$ are coefficients, and the blood pressure estimation method of this invention preferably has a step for establishment of the coefficients.

$$EBP = \beta_1 \cdot P1 + \beta_2 \cdot P2 + \beta_3 \cdot P3 + \beta_0 \quad (7)$$

$$EBP = \beta_1 \cdot 1/P1 + \beta_2 \cdot P2 + \beta_3 \cdot P3 + \beta_0 \quad (8)$$

Because coefficients $\beta_1$, $\beta_2$, $\beta_3$, and $\beta_0$ differ from an individual to an individual, it is desirable to determine the adjusted coefficients in advance by measuring actual blood pressure of the subject (measured blood pressure). Combinations of typical coefficients for each of conditions such as age, sex, body weight, and shape of pulse waves may be prepared in the device so that it can select a coefficient value typical for the input condition and apply to the calculation. The step for determination of coefficients $\beta_1$, $\beta_2$, $\beta_3$, and $\beta_0$ using measured blood pressure is performed as with one for determination of coefficients $\beta_1$, $\beta_2$, and $\beta_0$ in the formula (5) or (6); coefficients $\beta_1$, $\beta_2$, $\beta_3$, and $\beta_0$ are determined so that a change obtained by substitution of the measured parameter P1, parameter P2, and parameter P3 values into the formula (7) or (8) is approximated to that in measured blood pressure. Coefficient $\beta_0$ is required to estimate absolute blood pressure, but not required to calculate a relative change in blood pressure. In this case, a pre-determined fixed value B (0 [zero] for instance) may be used as coefficient $\beta_0$ instead of the estimated coefficient $\beta_0$ to calculate a relative change in blood pressure according to either formula, $EBP = \beta_1 \cdot P1 + \beta_2 \cdot P2 + \beta_3 \cdot P3 + B$ or $EBP = \beta_1 \cdot 1/P1 + \beta_1 \cdot P2 + \beta_3 \cdot P3 + B$ (B is a pre-determined value).

Device for the Blood Pressure Estimation

Figure 7:
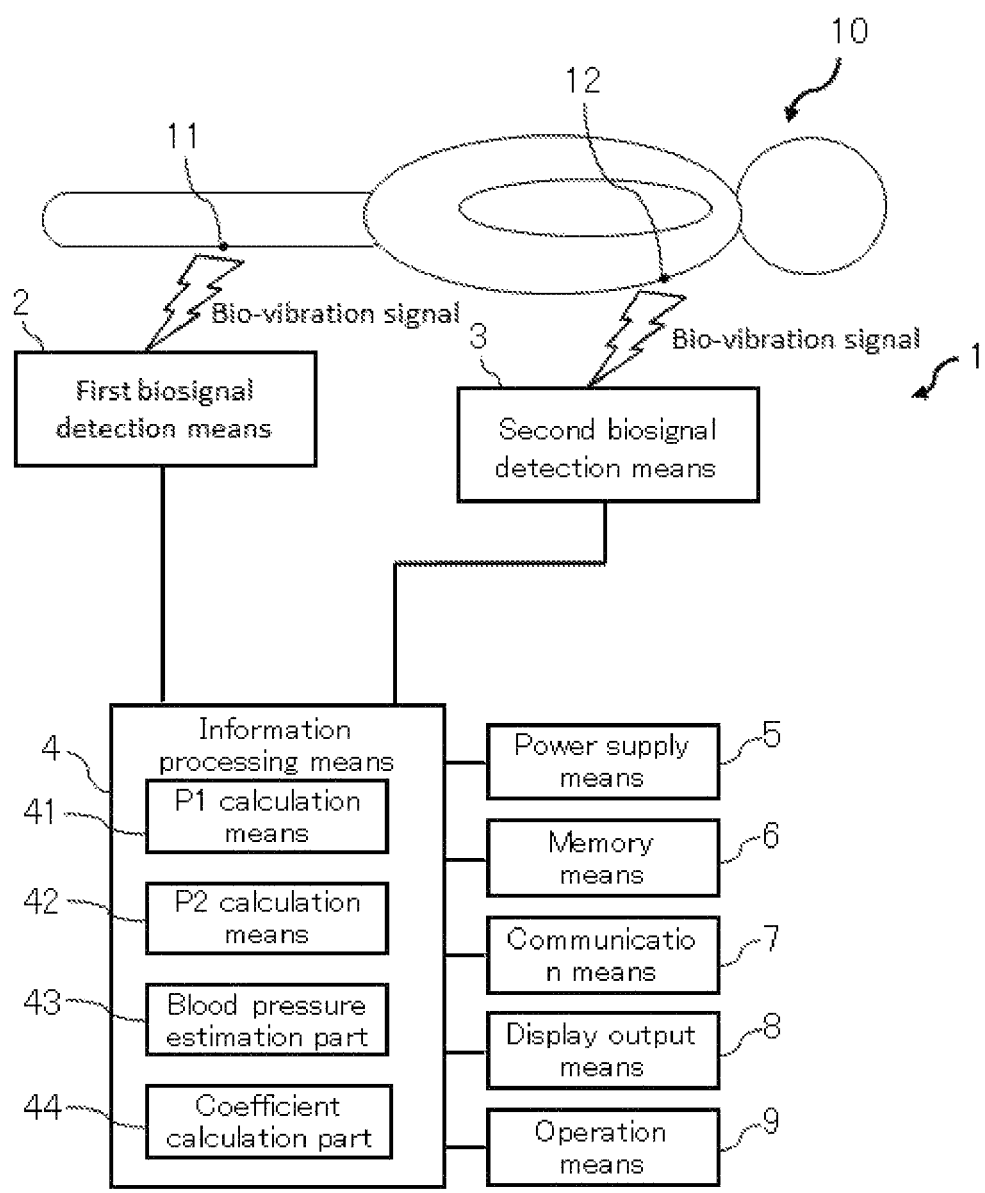
FIG. 7: Simple block diagram of device for the blood pressure estimation of this invention.

FIG. 7 shows a simple block diagram of the device for the blood pressure estimation 1 to realize the blood pressure estimation method of this invention. The device for the blood pressure estimation 1 is equipped with the first biosignal detection means 2 and second biosignal detection means 3 that can detect biosignals in a subject 10, and biosignals obtained through the first biosignal detection means 2 and second biosignal detection means 3 are input into the information processing device 4. The information processing device 4 may have the PTT-related parameter P1 calculation means 41; the stroke volume-related parameter P2 calculation means 42; the blood pressure estimation part that estimates blood pressure using parameter P1 and parameter P2; and the coefficient calculation part 44 that calculates coefficients $\beta_1$, $\beta_2$, and $\beta_0$. The device for the blood pressure estimation 1 may be provided with one or more of the power supply means 5, memory means 6, communication means 7, display output means 8, and operation means 9 where necessary. Furthermore, it may be additionally provided with a cuff-type blood pressure sensor that can continuously measure blood pressure for reference to determine coefficients and specified duration for PSA. In the case where SBP is estimated according to the formula (7) or (8) using parameter P3, which is related to SYS based on pulse waves, the information processing device 4 may additionally have the parameter P3 calculation means; the blood pressure estimation part that estimates blood pressure using parameter P1, parameter P2, and parameter P3; and the coefficient calculation part that calculates coefficients $\beta_1$, $\beta_2$, $\beta_3$, and $\beta_0$. The subject 10 is expressed as a human, but this device may be applied to not only humans but also the other animals.

The first biosignal detection means 2 and second biosignal detection means 3 acquire biosignals from the subject 10, more specifically, from multiple sites 11 and 12 of the subject 10. At least either of the biosignal detection means is a pulse wave sensor that acquires biosignals including pulse waves. The other may be a pulse wave sensor that acquire biosignals including pulse waves at a different site or a sensor that detects heart beats, for instance, a sensor for ECG, ballistocardiograph, or heart sound. Furthermore, the other biosignal detection means may be included to calculate multiple PTT and PSA values for improved accuracy. Terms "first and second" for the biosignal detection means 2 and 3 are only used to distinguish between two detection means for convenience.

The measurement sites 11 and 12 to which biosignal detection means are attached should be any position where at least the mean can detect heartbeats if applicable, but desirable sites may be the trunk (the body except for extremities), torso, or chest. A detection site of pulse waves is not particularly specified, but pulse waves may be acquired from the head, neck, lumbar region, buttock, upper-arm, forearm, hand, finger, leg, or volar. Especially, at least one biosignal detection means that detects pulse waves is desired to acquire the biosignals at a site apart from the heart, for instance, the extremity. If at least one biosignal detection means is a wearable sensor that can be attached to a subject, it would be desirable because the subject would neither feel stress owing to the burden nor be restrained. It is preferable that the wearable sensor is implemented on a component attached to the human extremity or head. For instance, of the upper limb of a subject, the finger, wrist, and arm are desirable body parts for attachment, and the sensor can be implemented on a ring, bracelet, fingerstall, wristband, etc. Of the lower limb of a subject, the thigh, calf, and ankle are desirable body parts for attachment. For instance, the sensor may be implemented on a band, sock, spats, etc. Of the head of a subject, the neck, temple, and ear are desirable body parts for attachment. For example, the sensor may be implemented on a head band, necktie, necklace, pierced earring, etc. Furthermore, the torso of a subject is an acceptable body part for attachment. For instance, the sensor may be implemented on a belt, belly band, clothes, etc.

The device for the blood pressure estimation 1 of this invention may acquire biosignals including the first set of pulse waves from the extremity through the first biosignal detection means 2 and also acquire biosignals including heart beats or the second set of pulse waves from the trunk (the body except for extremities) or torso through the second biosignal detection means 3. In addition, the device for the blood pressure estimation 1 of this invention may acquire biosignals including the first set of pulse waves from the extremity through the first biosignal detection means 2 and also acquire biosignals including the second set of pulse waves from the other extremity through the second biosignal detection means 3. More specific modality of the device for the blood pressure estimation 1 of this invention may be, for instance, described as follows: the first biosignal detection means 2 that acquires biological information including pulse waves is placed on the seating surface of a chair or the floor where the feet of a subject seating the chair are reached; and the second biosignal detection means 3 that acquires biological information about heartbeats is placed on the backrest of the chair. Furthermore, the device may be arranged on the seat of a vehicle such as a car for blood pressure estimation. For instance, the first biosignal detection means 2 and 3 may be included in the seating surface of a seat to acquire biological information including the first set of pulse waves from the buttock, and the second biosignal detection means 3 may be placed on the calf, backrest, head, steering wheel, etc. Similarly, in a wheelchair, the biological detection means may be placed in the seating surface, foot part, and backrest, and thus a wheelchair equipped with the device for the blood pressure estimation 1 can be provided. In addition, more specific modality of the device for the blood pressure estimation 1 of this invention other than the above may be, for instance, described as follows: the first biosignal detection means 2 and second biosignal detection means 3 are separately placed on or under the bedding such as a bed, mattress, and futon to acquire biosignals from a human lying in the bed. For instance, the first biosignal detection means 2 that acquire biological information including pulse waves may be placed under the chest of a human in the bed, and the second biosignal detection means 3 may be placed on the calf, lumbar region, or foot. In addition, more specific modality of the device for the blood pressure estimation 1 of this invention other than the above may be, for instance, described as follows: a wristband, belt, watch, ring, or headband equipped with the first biosignal detection means 2 is placed to acquire biosignals including pulse waves from the extremity, and the other one equipped with the second biosignal detection means 3 is directly applied to the torso or attached to the clothes in contact with the torso to collect biosignals including heartbeats or the second set of pulse waves.

For the biosignal detection means 2 and 3, the measurement method is not specified and thus may be either contact or non-contact type. A contact-type sensor can detect biosignals when placed in direct or indirect contact with a subject. A contact type biosignal detection means 2 and 3 can use, for instance, a vibration sensor that detects vibrations. If the sensor is placed in direct contact with or near a subject and can detect biological vibrations as electric signals, pulse waves or ballistocardiograph can be acquired. For a sensor for measurement of vibrations, a piezoelectric element is desirably used as a piezoelectric sensor, but a microphone that converts vibrations into electric signals may be used. Piezoelectric element materials may be ceramics or organic polymers. Desirable ceramic materials may be high-ε ferroelectric materials such as PZT and BST. Appropriate organic polymers may be, for instance, polyolefin materials, more specifically, such as porous polypropylene electret film (electro mechanical film, EMFI), polyvinylidene difluoride film (PVDF), poly[(vinylidenefluoride-co-trifluoroethylene] (P (VDF-TrFE)), and poly[(vinylidenefluoride-co-tetrafluoroethylene] (P (VDF-TFE)). The piezoelectric sensor is desirably in a film form and flexible. Furthermore, the piezoelectric sensor is desirable, because it is capable of acquiring biosignals without restraining the subject, allowing measurement in a more stress-free state. The piezoelectric sensor, however, may be used as a wearable sensor attached to a wristband, belt, watch, ring, or headband. In addition, a desirable microphone is small, for instance, in a diameter of approximately 10 mmφ or smaller.

A piezoelectric sensor in a flexible film form can be placed without feeling of restriction or oppression. The sensor electrode layer or electromagnetic shielding layer, therefore, desirably consists of soft materials such as thin electric conductive carbon membrane and silver electrode but not conventional aluminum. An example of the manufacturing process of a piezoelectric sensor is described below. Firstly, of a piezoelectric element material in a thin-sheet film form (for instance, PVDF in approximately 40 μm thickness), both sides are thoroughly covered with an electrode layer (for instance, an electric conductive carbon membrane in approximately 10 μm thickness) to form the electrode layers on both sides of the piezoelectric element material. Then, this electrode layers on both sides are laminated with an insulating membrane layer (for instance, polyethylene terephthalate [PET] film in approximately 20 μm thickness) to form the insulating layers on both sides. Furthermore, the insulating layers on both sides are covered with an electric conductive electromagnetic shielding layer (for instance, an electric conductive carbon membrane in approximately 10 μm thickness) to form the electromagnetic shielding layers on both sides. Finally, the electromagnetic shielding layers are laminated with a protective layer (for instance, PET film) to obtain a piezoelectric sensor in a sheet form. Because the sheet sensor device structured as above uses the soft electric conductive carbon membrane as a material comprised in the electrode layer and electromagnetic shielding layer, the sensor itself can be made flexible and thus can be attached to a wristband, belt, watch, ring, or headband without feeling of an unpleasantness. Other than the carbon materials, a silver electrode in 100 to 200 nm thickness may be used. Materials and manufacturing method of each layer are not limited to the above example.

In addition, the other type of the biosignal detection means 2 and 3 may be used to acquire biosignals: for instance, a highly sensitive accelerometry sensor may be attached in contact with the body like a watch or portable terminal; an accelerometry sensor may be integrated in a part of a bed or chair; and a pressure sensor that detects changes in air or liquid pressure in a tube may be used. Furthermore, as the biosignal detection means 2 and 3, a non-contact type sensor that can acquire biosignals in a non-contact fashion through signal transmission of microwaves, etc. may be used. The sensor may use the following signal transmission modalities: microwaves measured based on Doppler phenomenon, ultrawide band (UWB), electromagnetic waves other than microwaves, reflected or transmitted beam using LED light, and reflected waves using ultrasonic waves. These sensors using microwaves, etc. can be downsized and capable of acquiring signals in a non-contact and non-restraint manner under a remote operating condition. In addition, accelerometry sensors can be downsized as well. In addition, for a sensor for ECG measurement, dedicated electronic circuits are desirably affixed to the chest of the body using disposable electrodes, which measure ECG wave forms. Either unipolar or bipolar leads may be used for leading.

The sampling frequency of the biosignal detection means 2 and 3 is ≥500 Hz, preferably ≥1 kHz. Depending on a measurement position of pulse waves, when pulse waves are acquired from the buttock through the first biosignal detection means 2 placed in the seat, the distance between the heart and buttock is approximately 40 cm, and PAT will be 40 ms at the PWV of 10 m/s. Where, the sampling frequency of 500 Hz provides the resolution of 2 ms, and that of 1 kHz provides the resolution of 1 ms. The sampling frequency of ≥500 Hz, desirably ≥1 kHz, can improve the detection accuracy of PAT. This invention can be used at the sampling frequency of ≤500 Hz, if the measurement position for pulse waves is far from the heart or if high accuracy is not needed.

The information processing means 4 is connected with the biosignal detection means 2 and 3 in a wire or wireless mode and processes biosignals input from the biosignal detection means 2 and 3. The information processing means 4 in FIG. 7 is equipped with the P1 calculation means 41, P2 calculation means 42, blood pressure estimation part 43, and coefficient calculation part 44, but may additionally have the A/D converter, noise-reduction part, and signal processing part. The information processing means 4 can use, for instance, an electronic circuit or processing function of a central processing unit (CPU), and thus CPU in a mobile phone, smartphone, personal computer, server, cloud computing, etc. may be used as the information processing means 4. is a means that processes input bio-vibration signals. For example, an electronic circuit or processing function of a central processing unit (CPU) may be used for the processing. Based on the processing function of CPU, frequency filtering can be achieved, for instance, with digital filter. In addition, the information processing means 4 can be achieved with an analog circuit as well, but not a digital circuit. For instance, frequency filtering may be achieved with an analog filter such as low-pass filter (LPF) and high-pass filter (HPF) consisting of condenser, resistance, and operational amplifier. The input biosignals in an analog format, where applicable, may be converted into digital signals through analog-digital conversion circuit.

The power supply means 5 has a function to supply power to each part of the device for the blood pressure estimation 1. For instance, battery such as lithium ion battery may be employed. The memory means 6 has a function to store biosignals acquired with the biosignal detection means 2 and 3, results from calculation in the information processing means 4 (P1, P2, EBP, coefficients, etc.), and programs for operation of the information processing means 4. For instance, memory may be employed.

The communication means 7 has a function to receive and transmit various signals through wired or wireless communication. The communication means 7 may be wire or cable connected to the biosignal detection means 2 and 3. The wireless communication means 7 may send, for instance, biosignals acquired with the v biosignal detection means 2 and 3 to the information processing means 4, memory means 6, display output means 8, and external devices (not shown in the figure), send information such as P1, P2, and blood pressure calculated with the information processing means 4 to the memory means 6, display output means 8, and external devices (not shown in the figure), or send biosignals stored in the memory means 6 to the information processing means 4 and display output means 8. The communication means 7 may send information input by user through the operation means 9 to the information processing means 4, memory means 6, and display output means 8. For the wireless communication means 7, for instance, Bluetooth (trademark), Wi-fi (trademark), or near field radio communication (NFC) is desirable. In addition, the communication means 7 does not necessarily have a two-way communication function depending on the modality of the device for the blood pressure estimation 1.

The display output means 8 has a function to display or output calculation results from calculation (P1, P2, and blood pressure, etc.), various information input by the user, and details of the operation. For the display output means 8, a display, smartphone, or tablet device that shows calculation results in image may be employed. In addition, a printer that outputs calculation results in paper or a speaker that outputs calculation results in voice may be employed. The device for the blood pressure estimation 1 may be provided with a display, which is used as the display output means 8. In addition, the display output means 8 may display an alert or issue an alarm when the estimated blood pressure exceeds the pre-determined upper limit or drops below the pre-determined lower limit, or send such notice to an external device through the communication means 7.

The operation means 9 consists of a switch, touch panel, button, knob, keyboard, mouse, and voice input microphone to operate the device for the blood pressure estimation 1. If the display output means 8 consists of a touch panel that can response to user's operations, the operation means 9 may be designed to serve as the display output means 8, too.

Estimation of Blood Pressure Based on Pulse Waves at the Buttock and Calf

A piezoelectric sensor in a sheet form having an area of approximately 30 $cm^2$ was placed on the sheet of a chair as the biosignal detection means 2 to measure pulse waves at the buttock of the subject, and another piezoelectric sensor in a sheet form having a size of approximately 20 cm×5 cm was wrapped around the calf of the subject as the biosignal detection means 3 to measure pulse waves at the calf of the subject. When the sensor is wrapped around the calf to measure pulse waves, the sensor should be flexible not to give the calf feeling of restriction or oppression. For this purpose, thin electric conductive carbon membranes were used as the sensor electrode layer and electromagnetic shielding layer but not conventional aluminum material.

Furthermore, electrodes were attached to the chest to obtain ECG through bipolar leads as the reference data and for verification, and blood pressure was measured at the index finger with a volume-compensated sphygmomanometer. The measurement took 3 minutes. At 30 to 60 seconds after start of the measurement, the subject performed handgrip exercise, and during the first half of the measurement period or the first 90 seconds (including time for handgrip exercise), the coefficients were estimated. During the latter half or the subsequent 90 seconds, EBP was verified. The electrodes used to measure ECG can be used as the third biosignal detection means.

Figure 8:
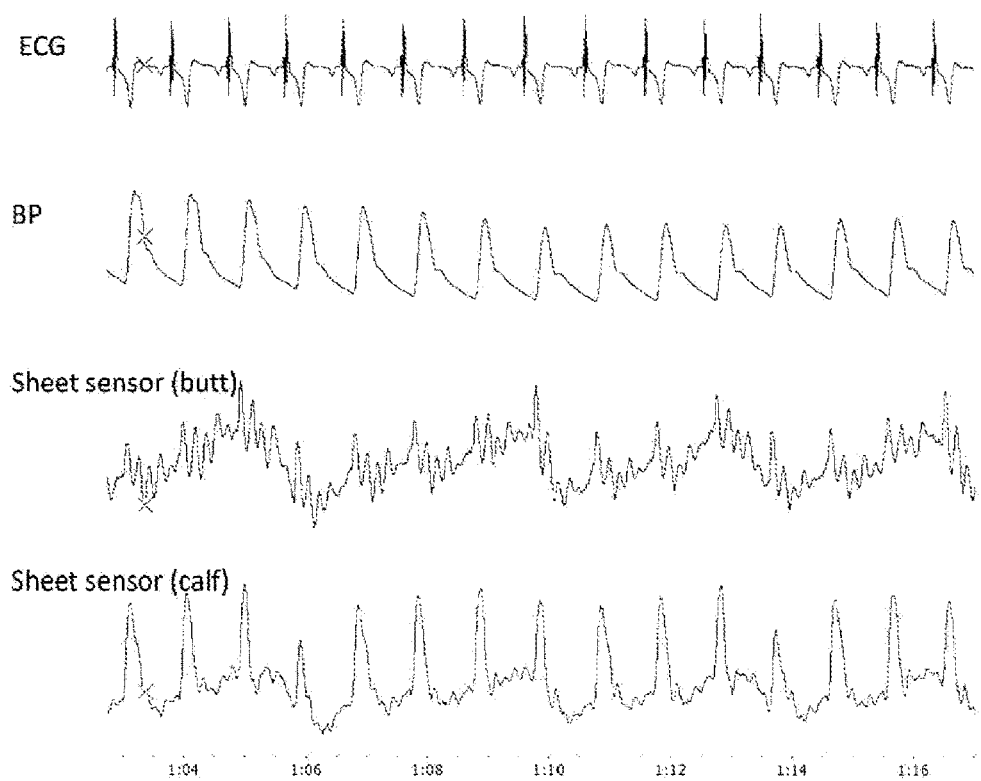
FIG. 8: ECG, measured blood pressure (BP), buttock pulse waves (butt), and calf pulse waves (calf).

FIG. 8 shows raw signals of ECG, measured blood pressure (BP), buttock pulse waves (butt), and calf pulse waves (calf) from the top. Because signals obtained as buttock pulse waves (butt) and calf pulse waves (calf) include not only pulse waves but also vibration components based on respiratory and body movements, it is desirable to perform signal processing to remove these noises. In addition, to identify the peaks and foot points in signal waveforms, signals obtained at each site may be subjected to processing procedures such as integration, differentiation, and Hilbert transformation.

Figure 9:
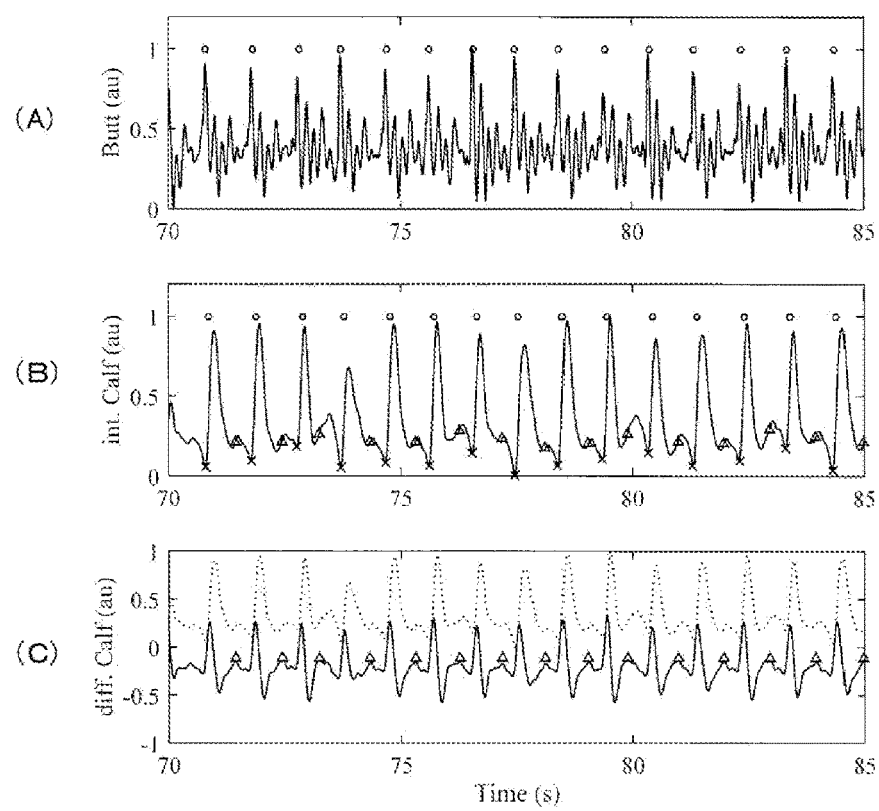
FIG. 9: (A) Signal processed buttock pulse waves (Butt); (B) calf integrated pulse waves (int. Calf); and (C) calf derivative pulse waveforms.

FIG. 9 (A) shows processed signals of buttock pulse waves (butt) obtained after a high-pass filter that passes frequencies ≥1 Hz; FIG. 9 (B) shows processed signals of calf pulse waves (calf) obtained after a high-pass filter and integration with respect to an attenuation time constant of 0.15 seconds; and FIG. 9 (C) shows integrated waveforms (top, dotted line) of calf pulse waves (calf) and differentiated waveforms (bottom, solid line) of calf pulse waves. In FIGS. 9 (A) and (B), circles at a level of 1 on the vertical axis indicate the position of the peak. PTT was calculated from a time difference between the peak positions. In addition, in FIG. 9 (B), crosses (x) on the waveforms indicate the position of the foot point, and triangles (Δ) on the waveforms indicate the position of the peak of a differentiated waveform from its trough to the next pulse. Using the position of Δ as DN, area under the curve from x to Δ of an integrated waveform of calf pulse waves (calf) in Figure (B) was calculated as PSA. Although a time constant of 0.15 seconds was used for integration of pulse waves to calculate PSA, an attenuation time constant may be changed within a range from 0.05 to 0.3 seconds according to the waveform of pulse waves, which differs depending on the measurement site of pulse waves. In FIG. 9, PSA was calculated based on calf pulse waves (calf), of which waveform was more stable than that of buttock pulse waves (butt), but PSA may be calculated based on buttock pulse waves (butt) or the total PSA or mean for both calf pulse waves (calf) and buttock pulse waves (butt) may be used. The information processing means may be designed to compare waveforms of pulse waves between the measurement sites and thereby calculate PSA based on pulse waves at one site of which waveform is more stable than that at the other site. For instance, correlation of waveforms of multiple peaks within a pulse wave may be investigated, and more correlated pulse waves may be selected as ones of which waveform is more stable.

Figure 10:
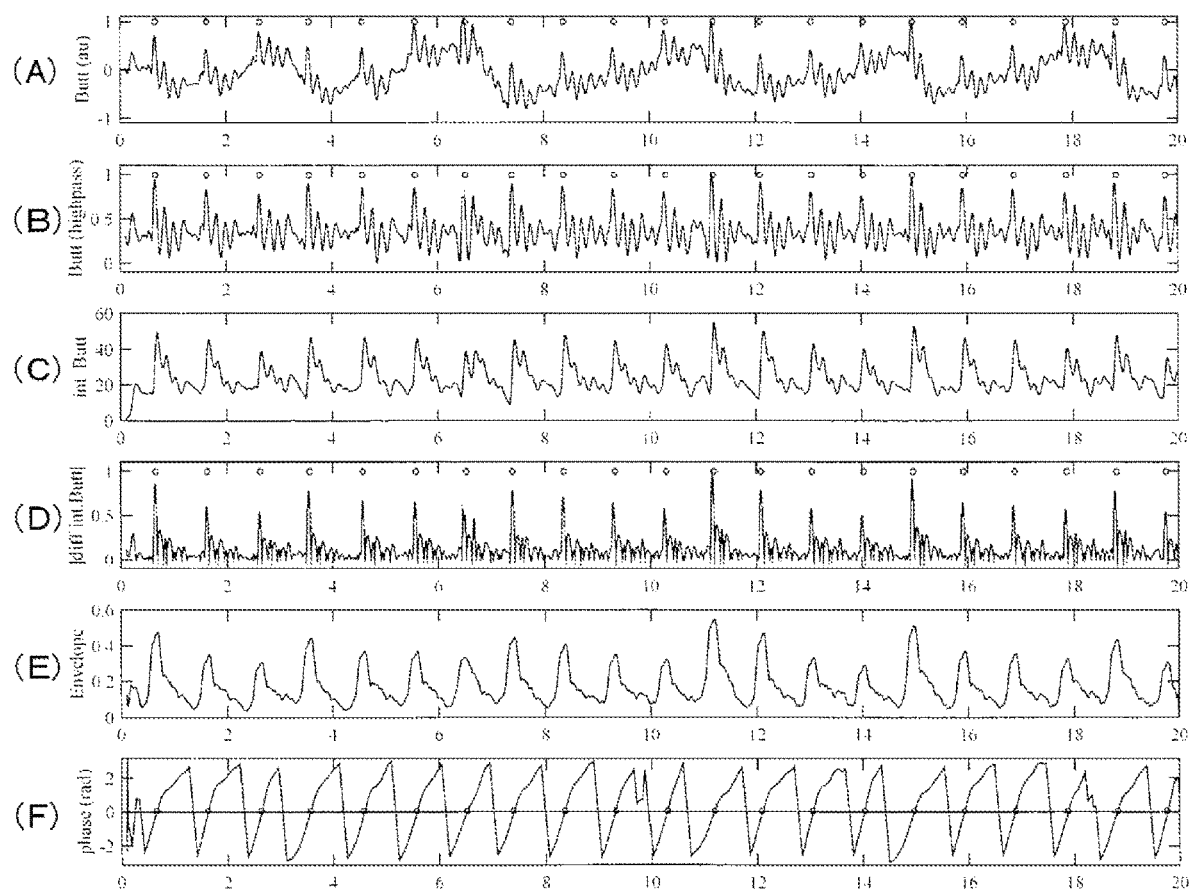
FIG. 10: Signal processing sequence to identify peak positions of buttock pulse waves (Butt).

FIG. 10 shows a sequence of signal processing to identify peaks in buttock pulse waves (butt). FIG. 10 (A), the top figure, shows raw signals of buttock pulse waves (the same as buttock pulse waves (butt) in FIG. 8) of which waveforms greatly wind owing to effects of respiratory signals. FIG. 10 (B) shows processed signals obtained by passing waveforms in (A) through a ≥1 Hz high-pass filter (the same as FIG. 9 (A)). Because low frequency signals below 1 Hz were removed from the waveforms (A), the waveforms no longer wind. The processed waveforms, however, present vibrations in which the peaks continuously attenuate. Although causes of these vibration waveforms remain unclear, repeated reflections of vibration waves associated with heartbeats in the chair under the buttock is considered to be responsible. The concerned vibration waveforms are not appropriate for determination of PSA and SYS. On the upper-arm and calf, on the other hand, repeated waves in such vibration waveforms are hardly observed. A potential reason for absence of such vibration waveforms is that vibration waves, for instance, from the upper arm are directly transmitted to a piezoelectric sensor without involving a reflecting medium. Waveforms from the buttock, accordingly, have to undergo signal processing for determination of PSA and SYS. To this signal processing, integration of waveforms in (B) with respect to a time constant may be applied. Waveforms in (C) are obtained by integration of ones in (B) with respect to a time constant of 0.15 seconds, and attenuating vibration waves have disappeared. Waveforms in (D) are obtained by differentiation of ones in (C) and conversion of the derivative values to absolute values. Figure (E) shows envelopes representative of amplitudes obtained by Hilbert transformation of waveforms in (D). Figure (F) shows instantaneous phases obtained by further Hilbert transformation of waveforms in (E). Waveforms in (C) and (E) can be used to determine PSA and SYS, because attenuating vibration waves have disappeared. In FIG. 10 (F), a timepoint where the waveform of an instantaneous phase crosses the axis of zero was identified as the peak position (circle in FIG. 9). In FIG. 9 (B), calf pulse waves (calf) were also subjected to similar signal processing to identify the peak positions.

Figure 11:
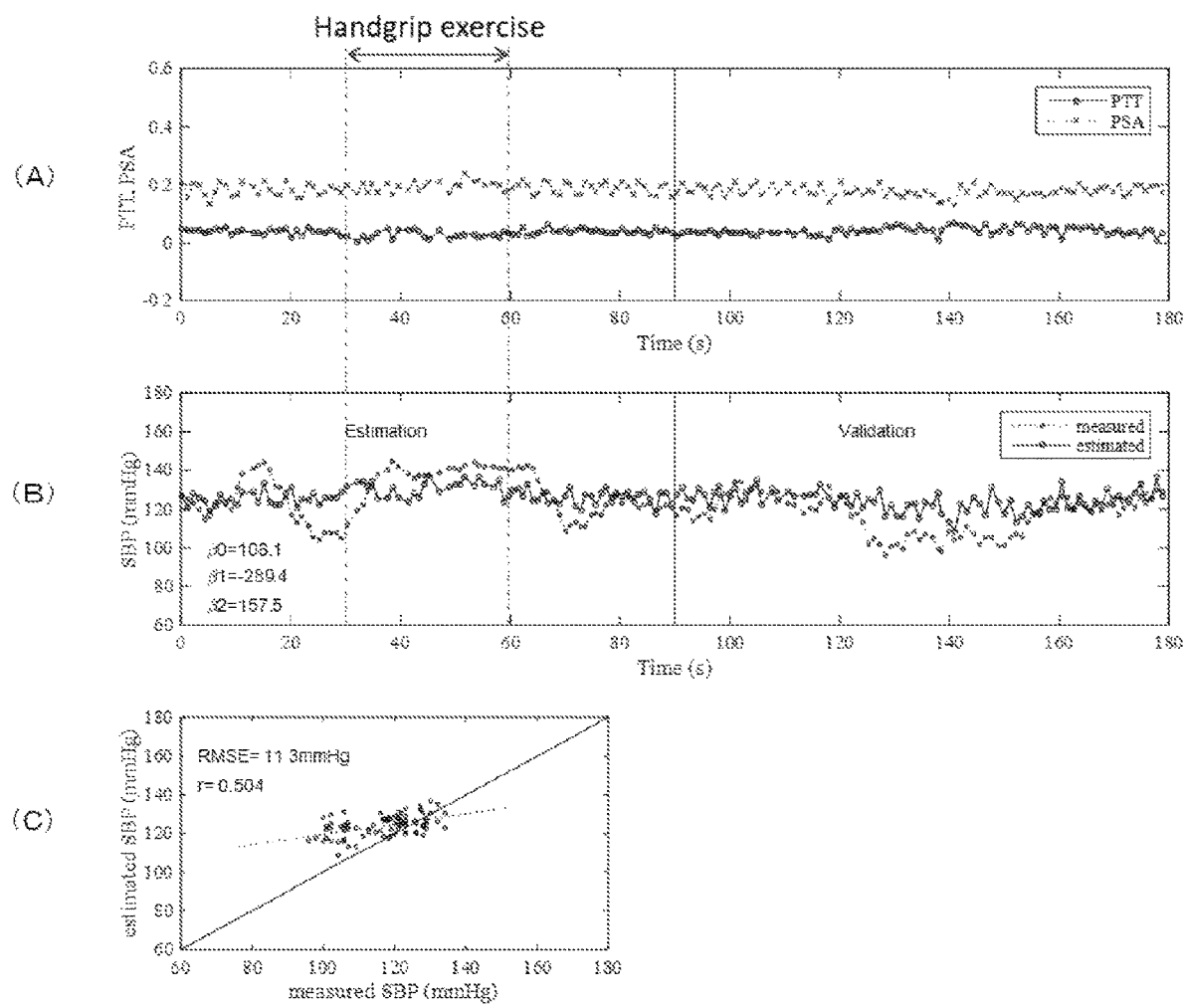
FIG. 11: (A) Relationship between PTT and area from x to Δ in a waveform (PSA) in FIG. 9 (B); (B) measured systolic blood pressure (dotted line) and estimated systolic blood pressure (EBP) (solid line); and (C) Correlation diagram between measured systolic blood pressure (horizontal axis) and estimated systolic blood pressure (vertical axis).

FIG. 11 (A) shows PTT between buttock pulse waves (butt) and calf pulse waves (calf) calculated from FIG. 9 and area from x to Δ in a waveform (PSA) in FIG. 9 (B). FIG. 11 (B) shows measured systolic blood pressure (dotted line) and estimated systolic blood pressure (EBP) (solid line) obtained according to the formula (5). As shown in FIGS. 11 (A) and (B), handgrip exercise was performed at 30 to 60 seconds after start of measurement to vary blood pressure. For data between 0 and 90 seconds in FIG. 11 (B), estimated systolic blood pressure (EBP) (solid line) is a result from approximation to measured SBP (dotted line) between 0 and 90 seconds by adjusting coefficients $\beta_1$, $\beta_2$, and $\beta_0$ based on PTT and PSA measured in the same time series. That is, in the formula (5), measured SBP was substituted for EBP between 0 and 90 seconds in FIG. 11 (B), and measured PTT and PSA were substituted for parameter P1 and parameter P2, respectively. To establish the formula (5) wherever possible, coefficients $\beta_1$, $\beta_2$, and $\beta_0$ were adjusted. Thereby, the coefficients $\beta_1$, $\beta_2$, and $\beta_0$ were estimated for the subject. Coefficients $\beta_1$, $\beta_2$, and $\beta_0$ were determined to be—289, 157, and 10, respectively. Data between 90 and 180 seconds in FIG. 11 (B) are results from validation of the formula (5) using the above estimated coefficients $\beta_1$, $\beta_2$, and $\beta_0$. In this validation, measured PTT and area (PSA) between 90 and 180 seconds were substituted into the formula (5) (with the estimated coefficients $\beta_1$, $\beta_2$, and $\beta_0$) to calculate EBP (solid line). As shown in data between 90 and 180 seconds in FIG. 11 (B), waveforms of EBP (solid line) calculated according to the formula (5) are close to those of measured SBP, demonstrating that the formula (5) is capable of estimating blood pressure of a subject. FIG. 11 (C) shows a correlation diagram between measured blood pressure (horizontal axis) and estimated blood pressure (vertical axis), and the correlation coefficient (r) was 0.504 with root mean square error (RMSE) of 11.3 mmHg.

Estimation of Blood Pressure Based on Pulse Waves at the Upper-Arm and Calf

A piezoelectric sensor in a sheet form having a size of approximately 20 cm×5 cm was placed on the upper-arm of the subject as the biosignal detection means 2 to measure pulse waves at the upper-arm of the subject, and another piezoelectric sensor in a sheet form having a size of approximately 20 cm×5 cm was wrapped around the calf of the subject as the biosignal detection means 3 to measure pulse waves at the calf of the subject. Furthermore, electrodes were attached to the chest to obtain ECG through bipolar leads as the reference data and for verification, and blood pressure was measured at the index finger with a volume-compensated sphygmomanometer. The measurement took 3 minutes. At 30 to 60 seconds after start of the measurement, the subject performed handgrip exercise, and during the first half of the measurement period or the first 90 seconds (including time for handgrip exercise), the coefficients were estimated. During the latter half or the subsequent 90 seconds, EBP was verified. The electrodes used to measure ECG can be used as the third biosignal detection means.

Figure 12:
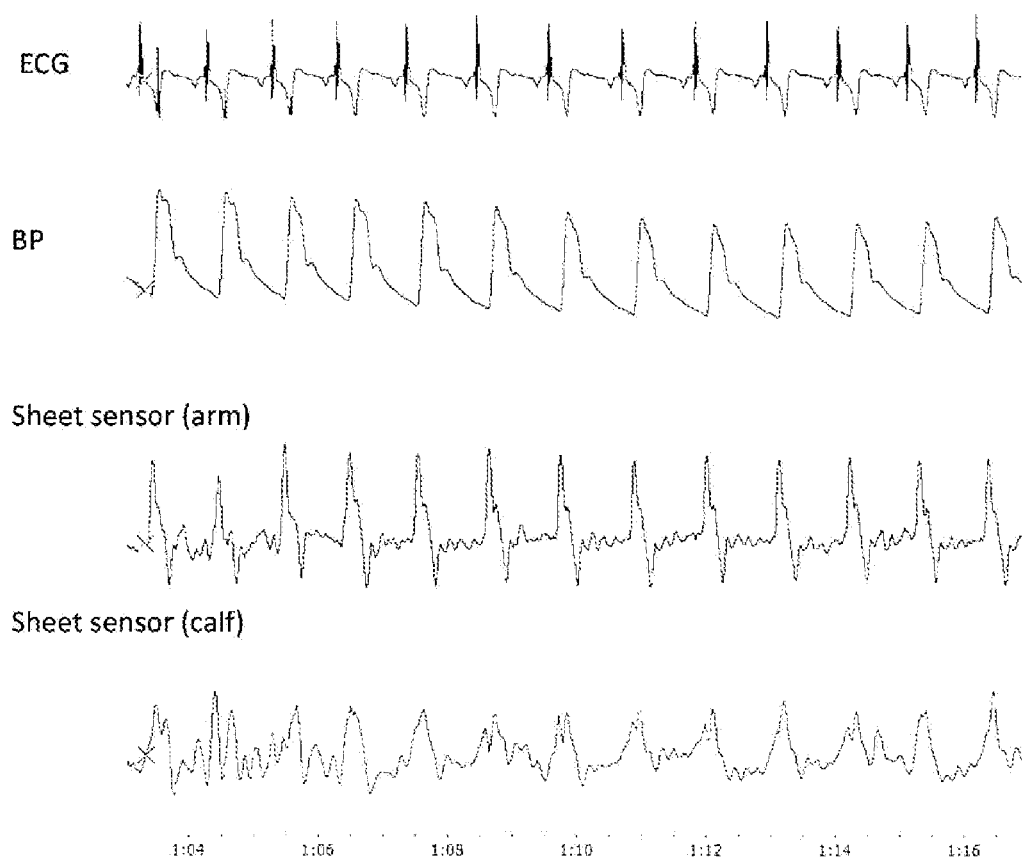
FIG. 12: ECG, measured blood pressure (BP), upper-arm pulse waves (arm), and calf pulse waves (calf).

FIG. 12 shows raw signals of ECG, measured blood pressure (BP), upper-arm pulse waves (arm), and calf pulse waves (calf) from the top. Because signals obtained as upper-arm pulse waves (arm) and calf pulse waves (calf) include not only pulse waves but also vibration components based on respiratory and body movements, it is desirable to perform signal processing to remove these noises. In addition, to identify the peaks and foot points in signal waveforms, signals obtained at each site may be subjected to processing procedures such as integration, differentiation, and Hilbert transformation.

Figure 13:
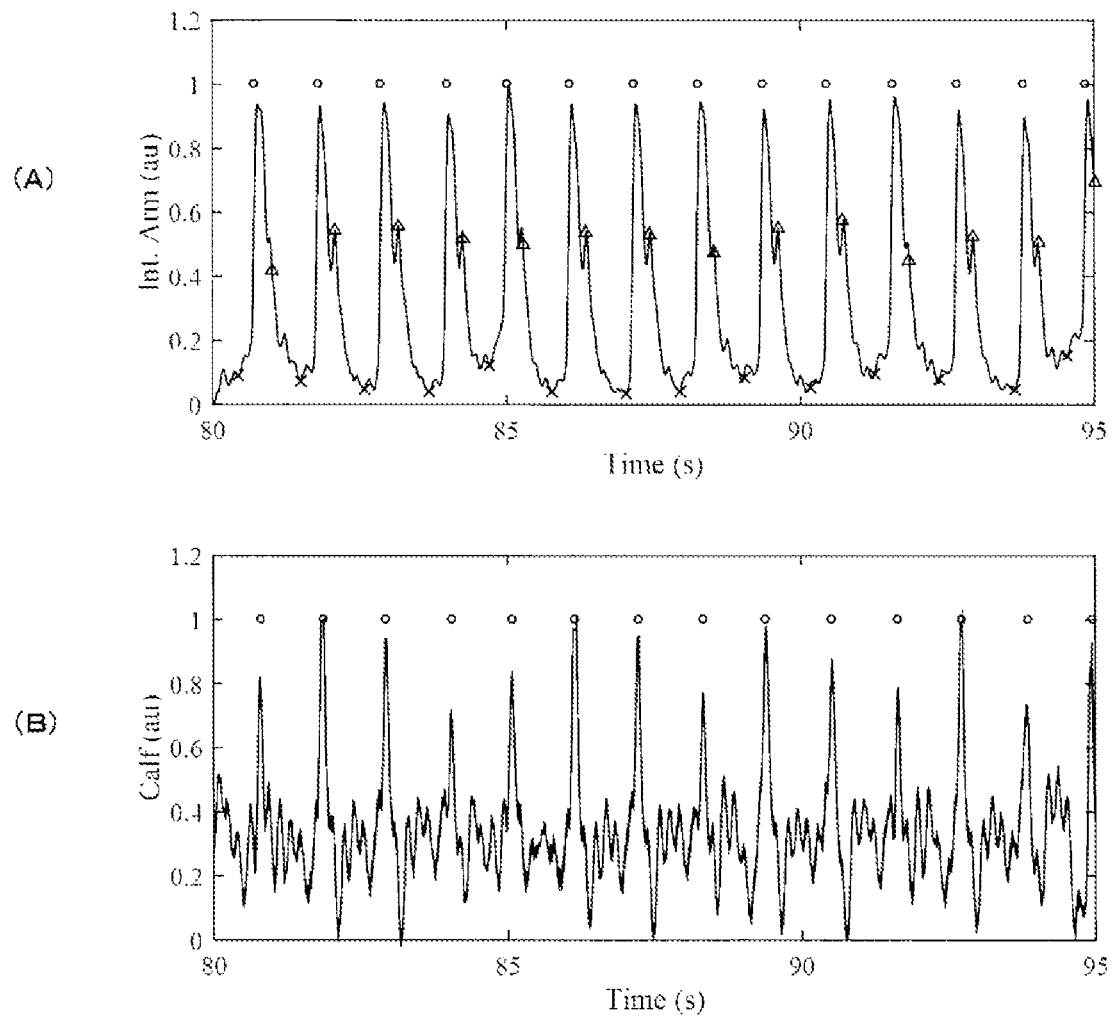
FIG. 13: Integrated waveforms of signal processed upper-arm pulse waves (Int Arm) and waveforms of calf pulse waves (Calf).

FIG. 13 (A) shows processed signals of upper-arm pulse waves (Int. Arm) obtained after a high-pass filter that passes frequencies ≥1 Hz and integration with respect to an attenuation time constant of 0.15 seconds; and FIG. 13 (B) shows processed signals of calf pulse waves (calf) obtained after a high-pass filter that passes frequencies ≥1 Hz. In FIGS. 13 (A) and (B), circles at a level of 1 on the vertical axis indicate the position of the peak. PTT was calculated from a time difference between the peak positions. In addition, in FIG. 13 (A), crosses (x) on the waveforms indicate the position of the foot point, and triangles (Δ) on the waveforms indicate the position of the maximum value (peak) on a differentiated waveform from its trough to the next pulse as with FIG. 9 (C). Using the position of Δ as DN, area under the curve from x to Δ of an integrated waveform of upper-arm pulse waves (Int. Arm) in FIG. 13 (A) was calculated as PSA. Although a time constant of 0.15 seconds was used for integration of pulse waves to calculate PSA, an attenuation time constant may be changed within a range from 0.05 to 0.3 seconds according to the waveform of pulse waves, which differs depending on the measurement site of pulse waves. In FIG. 13, PSA was calculated based on upper-arm pulse waves, of which waveform was more stable than that of calf pulse waves (calf), but PSA may be calculated based on calf pulse waves (calf) or the total PSA or mean for pulse waves at both positions may be used.

Figure 14:
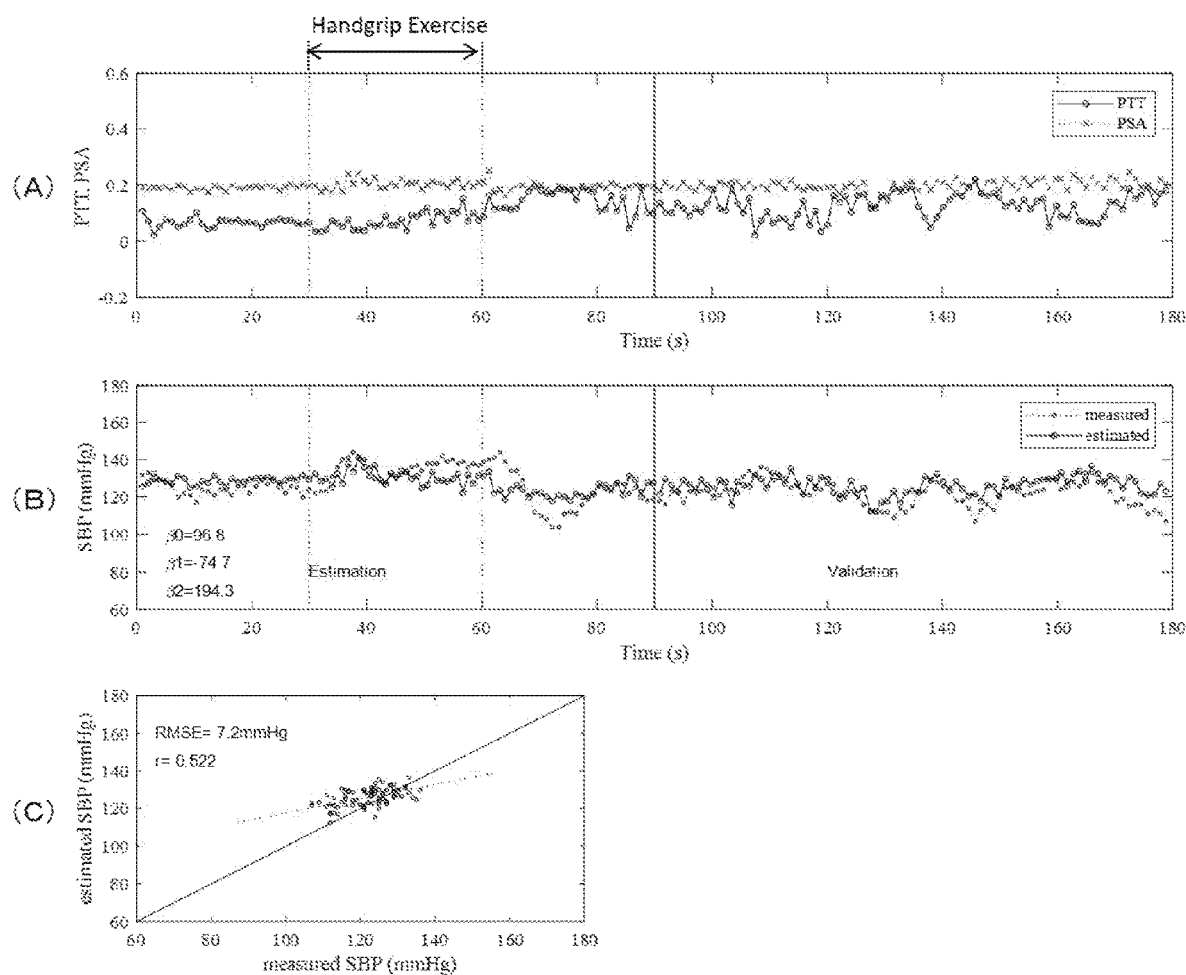
FIG. 14: (A) Relationship between PTT and area from x to Δ in a waveform (PSA) in FIG. 13 (A); (B) measured systolic blood pressure (dotted line) and estimated systolic blood pressure (EBP) (solid line); and (C) Correlation diagram between measured systolic blood pressure (horizontal axis) and estimated systolic blood pressure (vertical axis).

FIG. 14 (A) shows PTT between upper-arm pulse waves (arm) and calf pulse waves (calf) calculated from FIG. 13 and area from x to Δ in a waveform (PSA) in FIG. 13 (A). FIG. 14 (B) shows measured systolic blood pressure (dotted line) and estimated systolic blood pressure (EBP) (solid line) obtained according to the formula (5). As shown in FIGS. 14 (A) and (B), handgrip exercise was performed at 30 to 60 seconds after start of measurement to vary blood pressure. For data between 0 and 90 seconds in FIG. 14 (B), estimated systolic blood pressure (EBP) (solid line) is a result from approximation to measured SBP (dotted line) between 0 and 90 seconds by adjusting coefficients $\beta_1$, $\beta_2$, and $\beta_0$ based on PTT and PSA measured in the same time series. Coefficients $\beta_1$, $\beta_2$, and $\beta_0$ were determined to be—74.7, 194, and 96.8, respectively. Data between 90 and 180 seconds in FIG. 14 (B) are results from validation of the formula (5) using the above estimated coefficients $\beta_1$, $\beta_2$, and $\beta_0$. In this validation, measured PTT and area (PSA) between 90 and 180 seconds were substituted into the formula (5) (with the estimated coefficients $\beta_1$, $\beta_2$, and $\beta_0$) to calculate EBP (solid line). As shown in data between 90 and 180 seconds in FIG. 14 (B), waveforms of EBP (solid line) calculated according to the formula (5) are close to those of measured SBP, demonstrating that the formula (5) is capable of estimating blood pressure of a subject. FIG. 14 (C) shows a correlation diagram between measured systolic blood pressure (horizontal axis) and estimated systolic blood pressure (vertical axis), and the correlation coefficient (r) was 0.522 with root mean square error (RMSE) of 7.2 mmHg.

Figure 15:
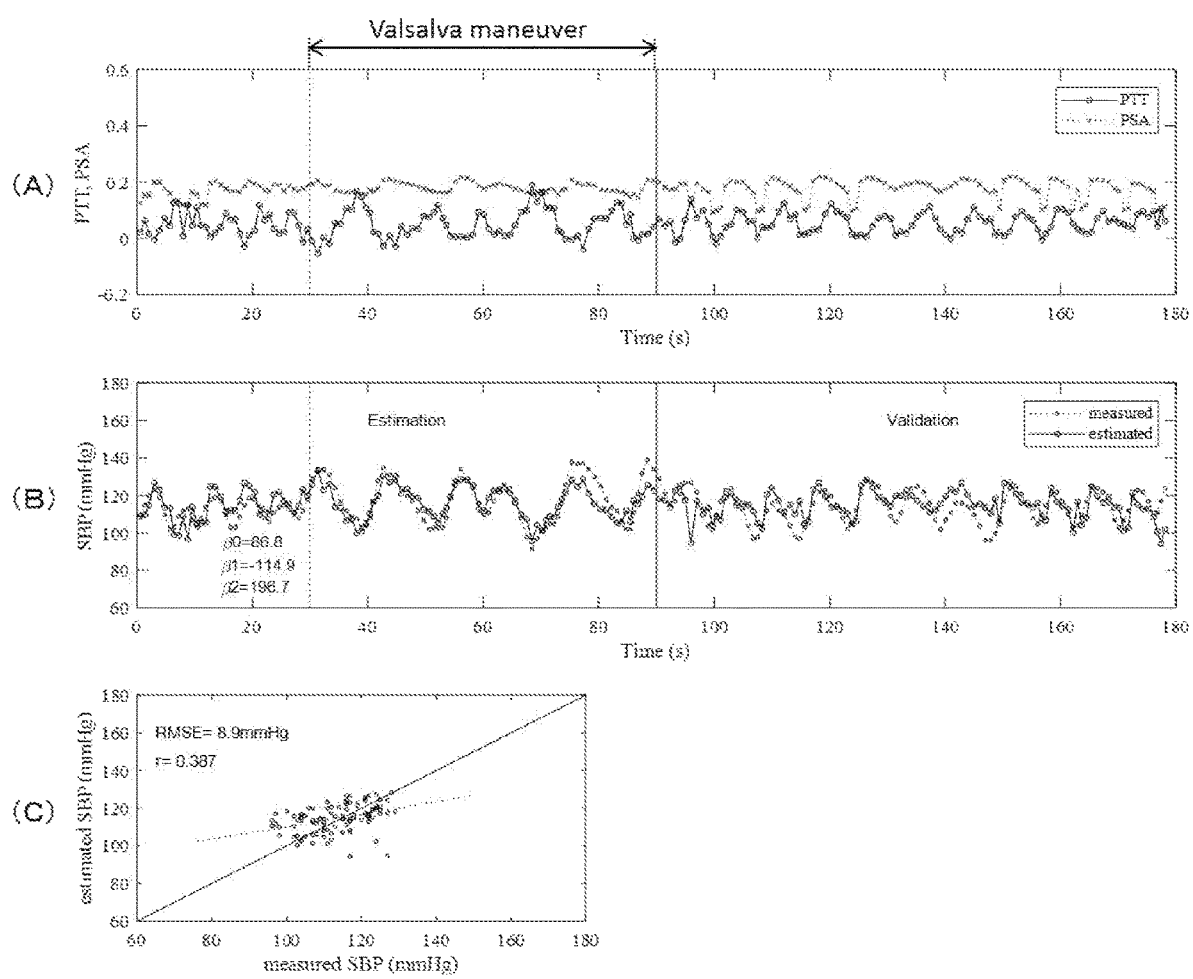
FIG. 15: (A) Relationship between PTT and PSA; (B) measured systolic blood pressure (dotted line) and estimated systolic blood pressure (EBP) (solid line); and (C) Correlation diagram between measured systolic blood pressure (horizontal axis) and estimated systolic blood pressure (vertical axis).

FIG. 15 (A) shows results from a subject who performed Valsalva maneuver instead of handgrip exercise to vary blood pressure. Pulse waves were measured at the upper-arm and calf. For data between 0 and 90 seconds in FIG. 15 (B), estimated systolic blood pressure (EBP) (solid line) is a result from approximation to measured SBP (dotted line) between 0 and 90 seconds by adjusting coefficients $\beta_1$, $\beta_2$, and $\beta_0$ based on PTT and PSA measured in the same time series. Coefficients $\beta_1$, $\beta_2$, and $\beta_0$ were determined to be—115, 197, and 86.8, respectively. Data between 90 and 180 seconds in FIG. 15 (B) are results from validation of the formula (5) using the above estimated coefficients $\beta_1$, $\beta_2$, and $\beta_0$. In this validation, measured PTT and area (PSA) between 90 and 180 seconds were substituted into the formula (5) (with the estimated coefficients $\beta_1$, $\beta_2$, and $\beta_0$) to calculate EBP (solid line). As shown in data between 90 and 180 seconds in FIG. 15 (B), waveforms of EBP (solid line) calculated according to the formula (5) are close to those of measured SBP, demonstrating that the formula (5) is capable of estimating blood pressure of a subject. FIG. 15 (C) shows a correlation diagram between measured systolic blood pressure (horizontal axis) and estimated systolic blood pressure (vertical axis), and the correlation coefficient (r) was 0.387 with root mean square error (RMSE) of 8.9 mmHg.

Figure 16:
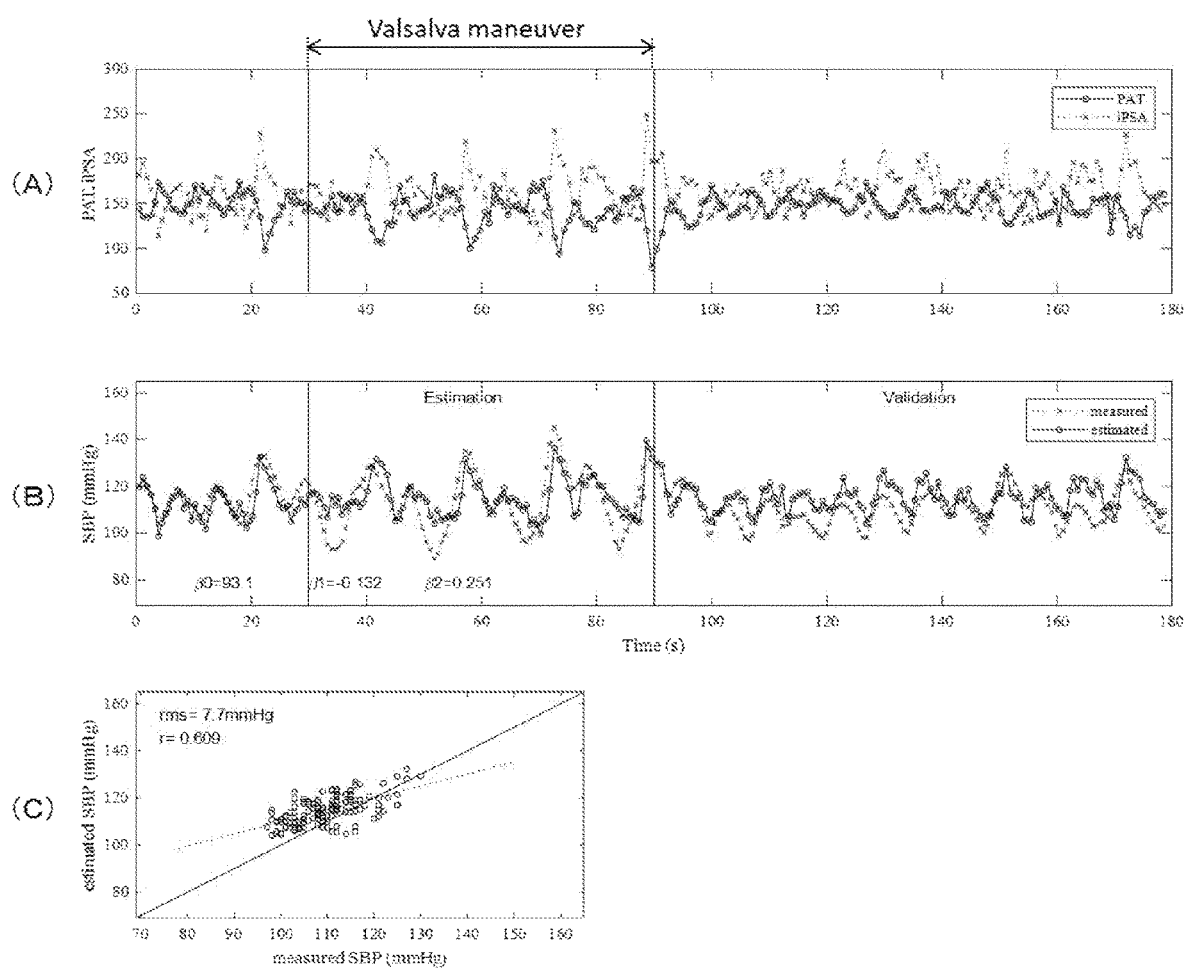
FIG. 16: (A) Relationship between PAT and ratio of PSA to mean area during the remaining period; (B) measured systolic blood pressure (dotted line) and estimated systolic blood pressure (EBP) (solid line); and (C) Correlation diagram between measured systolic blood pressure (horizontal axis) and estimated systolic blood pressure (vertical axis).

FIG. 16 shows results of blood pressure estimation using a ratio of the mean first area to the mean second area (iPSA, %) and pulse arrival time (PAT, ms), where PAT is a time difference between QRS wave in ECG and foot point of a calf pulse wave; the first area is PSA calculated based on a calf pulse wave; and the second area is an area during a part of the remaining period for the concerned pulse wave. For data between 0 and 90 seconds in FIG. 16 (B), estimated systolic blood pressure (EBP) (solid line) is a result from approximation to measured SBP (dotted line) between 0 and 90 seconds by adjusting coefficients $\beta_1$, $\beta_2$, and $\beta_0$ based on PTT and iPSA measured in the same time series. Coefficients β₁, β₂, and β₀ were determined to be—0.132, 0.251, and 93.1, respectively. Data between 90 and 180 seconds in FIG. 16 (B) are results from validation of the formula (5) using the above estimated coefficients $\beta_1$, $\beta_2$, and $\beta_0$. In this validation, measured PAT and iPSA between 90 and 180 seconds were substituted into the formula (5) (with the estimated coefficients $\beta_1$, $\beta_2$, and $\beta_0$) to calculate EBP (solid line). As shown in data between 90 and 180 seconds in FIG. 16 (B), waveforms of EBP (solid line) calculated according to the formula (5) are close to those of measured SBP, demonstrating that the formula (5) is capable of estimating blood pressure of a subject. FIG. 16 (C) shows a correlation diagram between measured systolic blood pressure (horizontal axis) and estimated systolic blood pressure (vertical axis), and the correlation coefficient (r) was 0.609 with root mean square error (RMSE) of 7.7 mmHg.

The device for the blood pressure estimation of this invention can be integrated in various ornaments and electronic devices. For instance, the biosignal detection means (for instance, piezoelectric sensor) may be integrated in a bracelet, watch, ring, collar, shoe, or earring to measure biosignals of the user. Furthermore, the biosignal detection means (for instance, piezoelectric sensor) may be directly applied to the body or attached to the clothes in contact with the body to measure biosignals. A communication means may be used to send biosignals acquired with the biosignal detection means to a portable terminal or computer, in which blood pressure is estimated. The device for the blood pressure estimation of this invention is capable of monitoring blood pressure in daily activity settings or during exercise. For instance, it can monitor the condition of drivers of automobiles, trains, and airplanes.

LEGEND

1 Device for the blood pressure estimation
2 First biosignal detection means
3 Second biosignal detection means
4 Information processing means
5 Power supply means
6 Memory means
7 Communication means
8 Display output means
9 Operation means
41 P1 calculation means
42 P2 calculation means
43 Blood pressure estimation part
44 Coefficient calculation part

The invention claimed is:

1. A blood pressure estimation method that estimates systolic blood pressure (EBP) of a subject by using an electronic or computer-mediated information processing means and an electronic or computer-mediated display output means in a real time basis without the use of a cuff, wherein:
(I) said information processing means calculates said estimated EBP according to the formula: EBP=β1·P1+β2·P2+β0 or EBP=β1·1/P1+β2·P2+β0, wherein β1, β2, and β0 are coefficients and P1 and P2 are variables, wherein:
(A) P1 is a parameter that is related to pulse transit time (PTT); and
(B) P2 is a parameter that is related to stroke volume based on pulse waves, wherein parameter P2 is a ratio of a mean first area of a pulsatile systolic area (PSA) of a pulse wave expressed in signal waveform to a mean second area of a remaining area of said pulse wave, and wherein:
(1) said PSA is defined by an area under the curve above a horizontal line extending through a foot point to a vertical line extending through a dicrotic notch (DN) of said pulse wave, and
(2) said remaining area is defined by a portion of an area under the curve from the vertical line extending through the DN and above the horizontal line of said pulse wave to a foot point of a next pulse wave; and
(II) said electronic or computer-mediated display output means outputs said calculated EBP to a display, issues an alarm if the calculated EBP exceeds a pre-determined upper limit or drops below a pre-determined lower limit, and/or sends such output to an external device;
wherein said blood pressure estimation method is capable of providing real-time blood pressure monitoring of said subject.

2. The blood pressure estimation method as defined in claim 1, wherein blood pressure measurements are obtained from the subject under varied loads, while values for parameter P1 and parameter P2 are measured; the measured values for parameter P1 and parameter P2 are then substituted into the formula to give coefficients β1, β2, and β0 that allow approximation of a change in measured blood pressure.

3. The blood pressure estimation method as defined in claim 1, wherein the DN is a position where slope of said pulse wave turns from negative to positive between a maximum point of said pulse wave and the foot point of the next pulse wave.

4. The blood pressure estimation method as defined in claim 1, wherein a change in relative systolic blood pressure (EBP) is calculated using the coefficient β0 as a pre-determined fixed value.

5. A blood pressure estimation method that estimates systolic blood pressure (EBP) of a subject by using an electronic or computer-mediated information processing means and an electronic or computer-mediated display output means in a real time basis without the use of a cuff, wherein:
(I) said information processing means calculates said estimated EBP according to the formula: EBP=β1·P1+β2·P2+β3·P3+β0 or EBP=β1·1/P1+β2·P2+β3·P3+β0 wherein β1, β2, β3, and β0 are coefficients and P1, P2 and P3 are variables, wherein:
(A) P1 is a parameter that is related to pulse transit time (PTT);
(B) P2 is a parameter that is related to stroke volume based on pulse waves, wherein P2 is a ratio of a mean first area of a pulsatile systolic area (PSA) of a pulse wave expressed in signal waveform to a mean second area of a remaining area of said pulse wave, and wherein:
(1) said PSA is defined by an area under the curve above a horizontal line extending through a foot point to a vertical line extending through a dicrotic notch (DN) of said pulse wave, and
(2) said remaining area is defined by a portion of an area under the curve from the vertical line extending through the DN and above the horizontal line of said pulse wave to a foot point of a next pulse wave; and
(C) P3 is a parameter that is related to systole duration based on pulse waves; and (II) said electronic or computer-mediated display output means outputs said calculated EBP to a display, issues an alarm if the calculated EBP exceeds a pre-determined upper limit or drops below a pre-determined lower limit, and/or sends such output to an external device;

wherein said blood pressure estimation method is capable of providing real-time blood pressure monitoring of said subject.

6. The blood pressure estimation method as defined in claim 5, wherein blood pressure measurements are obtained from the subject under varied loads, while values for parameter P1, parameter P2, and parameter P3 are measured; the measured values for parameter P1, parameter P2 and parameter P3 are then substituted into the formula to give coefficients $\beta_1$, $\beta_2$, $\beta_3$, and $\beta_0$ that allow approximation of a change in measured blood pressure.

7. The blood pressure estimation method as defined in claim 5, wherein the DN is a position where slope of said pulse wave turns from negative to positive between a maximum point of said pulse wave and the foot point of the next pulse wave.

8. The blood pressure estimation method as defined in claim 5, wherein a change in relative systolic blood pressure (EBP) is calculated using the coefficient $\beta_0$ as a pre-determined fixed value.

9. A device for blood pressure estimation, wherein said device comprises:
(A) a first biosignal detection means and a second biosignal detection means that detect biosignals on a subject; and
(B) an electronic or computer-mediated information processing means that comprises:
a P1 calculation means that calculates a parameter P1, which is related to pulse transit time (PTT), from biosignals acquired through the first biosignal detection means and second biosignal detection means; and
a P2 calculation means that calculates a parameter P2, which is related to stroke volume based on pulse waves, from biosignals acquired through either or both of the first biosignal detection means and second biosignal detection means; and
(C) an electronic or computer-mediated display output means;
wherein:
(I) said device estimates electronic or computer-mediated information processing means is capable of calculating said estimated systolic blood pressure (EBP) according to the formula: EBP=$\beta 1 \cdot$P1+$\beta 2 \cdot$P2+$\beta 0$ or EBP=$\beta 1 \cdot 1/$P1+$\beta 2 \cdot$P2+$\beta 0$, wherein $\beta 1$, $\beta 2$, and $\beta 0$ are coefficients and P1 and P2 are variables;
wherein P2 is a ratio of a mean first area of a pulsatile systolic area (PSA) of a pulse wave expressed in signal waveform to a mean second area of a remaining area of said pulse wave, and wherein:
(1) said PSA is defined by an area under the curve above a horizontal line extending through a foot point to a vertical line extending through a dicrotic notch (DN) of said pulse wave, and
(2) said remaining area is defined by a portion of an area under the curve from the vertical line extending through the DN and above the horizontal line of said pulse wave to a foot point of a next pulse wave;
and wherein the parameter P1 is calculated by the P1 calculation means and parameter P2 is calculated by the P2 calculation means; and (II) said electronic or computer-mediated display output means is capable of outputting said calculated EBP to a display, of issuing an alarm if the calculated EBP exceeds a pre-determined upper limit or drops below a pre-determined lower limit, and/or of sending such output to an external device.

10. A device for blood pressure estimation as defined in claim 9, wherein at least either of the first biosignal detection means and second biosignal detection means is a pulse wave sensor that acquires biosignals including pulse waves.

11. A device for blood pressure estimation, wherein said device comprises:
(A) a first biosignal detection means and second biosignal detection means that detect biosignals on a subject;
(B) an electronic or computer-mediated information processing means that comprises:
a P1 calculation means that calculates a parameter P1, which is related to pulse transit time (PTT), from biosignals acquired through the first biosignal detection means and second biosignal detection means;
a P2 calculation means that calculates a parameter P2, which is related to stroke volume based on pulse waves, from biosignals acquired through either or both of the first biosignal detection means and second biosignal detection means; and
a P3 calculation means that calculates a parameter P3, which is related to systole duration based on pulse waves from biosignals acquired through either or both of the first biosignal detection means and second biosignal detection means; and
(C) an electronic or computer-mediated display output means;
wherein:
(I) said electronic or computer-mediated information processing means is capable of calculating said estimated systolic blood pressure (EBP) according to the formula: EBP=$\beta_1 \cdot$P1+$\beta_2 \cdot$P2+$\beta_3 \cdot$P3+$\beta_0$ or EBP=$\beta_1 \cdot 1/$P1+$\beta_2 \cdot$P2+$\beta_3 \cdot$P3+$\beta_0$, wherein $\beta_1$, $\beta_2$, $\beta_3$, and $\beta_0$ are coefficients and P1, P2 and P3 are variables;
wherein P2 is a ratio of a mean first area of a pulsatile systolic area (PSA) of a pulse wave expressed in signal waveform to a mean second area of a remaining area of said pulse wave, and wherein:
(1) said PSA is defined by an area under the curve above a horizontal line extending through a foot point to a vertical line extending through a dicrotic notch (DN) of said pulse wave, and
(2) said remaining area is defined by a portion of an area under the curve from the vertical line extending through the DN and above the horizontal line of said pulse wave to a foot point of a next pulse wave;
and wherein the parameter P1 is calculated by the P1 calculation means, parameter P2 is calculated by the P2 calculation means, and parameter P3 is calculated by the P3 calculation means; and
(II) said electronic or computer-mediated display output means is capable of outputting said calculated EBP to a display, of issuing an alarm if the calculated EBP exceeds a pre-determined upper limit or drops below a pre-determined lower limit, and/or of sending such output to an external device.

12. The device for blood pressure estimation as defined in claim 10, wherein said pulse wave sensor is a piezoelectric sensor in a sheet form.

13. The device for blood pressure estimation as defined in claim 11, wherein at least one of the first biosignal detection means and second biosignal detection means is a pulse wave sensor that acquires biosignals including pulse waves.

14. The device for blood pressure estimation as defined in claim 13, wherein said pulse wave sensor is a piezoelectric sensor in a sheet form.

\* \* \* \* \*